United States Patent [19]
Kato et al.

[11] Patent Number: 5,939,615
[45] Date of Patent: Aug. 17, 1999

[54] METHOD OF MEASURING A GAS COMPONENT AND SENSING DEVICE FOR MEASURING THE GAS COMPONENT

[75] Inventors: Nobuhide Kato, Aichi-ken; Kunihiko Nakagaki, Nagoya, both of Japan

[73] Assignee: NGK Insulators, Ltd., Japan

[21] Appl. No.: 09/085,940

[22] Filed: May 28, 1998

Related U.S. Application Data

[63] Continuation of application No. 08/916,221, Aug. 22, 1997, Pat. No. 5,866,799, which is a continuation of application No. 08/681,363, Jul. 23, 1996, Pat. No. 5,672,811, which is a continuation-in-part of application No. 08/422,956, Apr. 17, 1995, abandoned.

[30] Foreign Application Priority Data

| Apr. 21, 1994 | [JP] | Japan | 6-83069 |
| Jan. 31, 1995 | [JP] | Japan | 7-14598 |
| Mar. 8, 1995 | [JP] | Japan | 7-48551 |
| Feb. 23, 1996 | [JP] | Japan | 8-36753 |

[51] Int. Cl.[6] .................................................. G01N 27/41
[52] U.S. Cl. .................... 73/31.05; 204/425; 204/426; 204/427
[58] Field of Search ................ 73/23.31, 31.05; 204/425, 426, 427

[56] References Cited

U.S. PATENT DOCUMENTS

| 4,645,572 | 2/1987 | Nishizawa et al. | 204/425 |
| 4,770,760 | 9/1988 | Noda et al. | 204/426 |
| 4,902,400 | 2/1990 | Usami et al. | 204/425 |
| 4,909,072 | 3/1990 | Logothetis et al. | 204/426 |
| 4,927,517 | 5/1990 | Mizutani et al. | 204/406 |
| 5,028,309 | 7/1991 | Nishizawa et al. | 204/425 |
| 5,034,112 | 7/1991 | Murase et al. | 204/406 |
| 5,049,254 | 9/1991 | Logothetis et al. | 204/425 |
| 5,080,765 | 1/1992 | Wang et al. | 204/425 |
| 5,089,113 | 2/1992 | Logothetis et al. | 204/425 |
| 5,145,566 | 9/1992 | Logothetis et al. | 204/427 |
| 5,217,588 | 6/1993 | Wang et al. | 204/426 |
| 5,250,169 | 10/1993 | Logothetis et al. | 204/425 |
| 5,288,375 | 2/1994 | Logothetis et al. | 204/425 |
| 5,304,294 | 4/1994 | Wang et al. | 204/427 |
| 5,602,326 | 2/1997 | Takahashi et al. | 73/23.31 X |
| 5,672,811 | 9/1997 | Kato et al. | 73/31.05 |
| 5,763,763 | 6/1998 | Kato et al. | 73/23.32 X |

FOREIGN PATENT DOCUMENTS

| 60944 | 9/1982 | European Pat. Off. |
| 257842 | 3/1988 | European Pat. Off. |
| 3924644 | 1/1991 | Germany . |
| 4311851 | 10/1994 | Germany . |
| 5-18059 | 10/1986 | Japan . |
| 63-38154 | 2/1988 | Japan . |
| 64-39545 | 2/1989 | Japan . |
| 1-27751 | 11/1989 | Japan . |
| 2-1543 | 1/1990 | Japan . |

*Primary Examiner*—Daniel S. Larkin
*Attorney, Agent, or Firm*—Wall Marjama Bilinski & Burr

[57] ABSTRACT

A method and a sensing device of measuring a concentration of a gas component of a measurement gas, which method includes the steps of: introducing the measurement gas containing the gas component, from an external measurement-gas space into a first internal space, under a diffusion resistance; controlling an amount of oxygen in the measurement gas within the first internal space, so as to produce an atmosphere which does not substantially affect measurement of the gas component and which does not convert the gas component; introducing the atmosphere from the first internal space into a second internal space, under a diffusion resistance; and measuring the concentration of the gas component present in the atmosphere in the second internal space.

4 Claims, 22 Drawing Sheets

METHOD OF MEASURING A GAS COMPONENT AND SENSING DEVICE FOR MEASURING THE GAS COMPONENT

This is a continuation of U.S. Ser. No. 08/916,221, filed Aug. 22, 1997, now U.S. Pat. No. 5,866,799, which in turn is a continuation of U.S. Ser. No. 08/681,363, filed Jul. 23, 1996, now U.S. Pat. No. 5,672,811, which in turn is a continuation-in-part of U.S. Ser. No. 08/422,956, filed Apr. 17, 1995, abandoned. All of the above-referenced applications are incorporated herein by reference.

BACKGROUND OF THE INVENTION

1. Field of the Invention

The present invention relates to a method and a sensing device for measuring a component contained in a measurement gas, and more particularly to methods and various gas sensors for determining the concentration of gas components containing bonded oxygen. In particular, the present invention is concerned with a sensor adapted for measuring the concentration of NOx as a component of a combustion gas, and a method for determining the NOx concentration.

2. Discussion of Related Art

Various measuring methods and devices have been proposed for determining the concentration of a desired gas component in a measurement gas. A known method of measuring NOx in combustion gases, for example, employs a sensor having an oxygen-ion conductive solid electrolyte, such as zirconia, and a Pt-containing electrode and a Rh-containing electrode formed thereon. This method utilizes the ability of Rh to reduce NOx, and determines the NOx concentration by measuring an electromotive force induced between the two electrodes. However, this sensor tends to suffer from noise, since the electromotive force varies to a great extent with a change in the concentration of oxygen contained in the combustion gases, but varies a small extent in response to a change in the NOx concentration. In addition, CO or other reducing gas is needed for the Rh electrode to reduce the NOx. Under a lean combustion condition using an excessively small amount of a fuel, a large amount of NOx is generated, which exceeds the amount of CO generated. Thus, the known sensor is not able to make a measurement with respect to a combustion gas produced under such a lean combustion condition.

There is also known a method of measuring NOx by using a pair of cells consisting of an electrochemical pumping cell and a sensing cell, which pair of cells include Pt electrodes and oxygen-ion conductive solid electrolyte, and another pair of cells consisting of an electrochemical pumping cell and a sensing cell, which another pair of cells include Rh electrodes and oxygen-ion conductive solid electrolyte, as disclosed in JP-A-63-38154 and JP-A-64-39545. The concentration of NOx is calculated based on a difference between pumping currents flowing through the respective pumping cells. In further methods as disclosed in JP-A-1-277751 and JP-A-2-1543, a first and a second pair of cells each consisting of an electrochemical pumping cell and a sensing cell are prepared, and a limiting current is measured by a sensor having the first pair of pumping and sensing cells, under the oxygen partial pressure that does not allow reduction of NOx, while a limiting current is measured by a sensor having the second pair of pumping and sensing cells, under the oxygen partial pressure which allows reduction of NOx, so as to measure the NOx concentration based on a difference between the limiting currents of the two sensors. It is also proposed to measure a difference in the limiting currents, using a sensor having a pair of pumping and sensing cells, by regulating the oxygen partial pressure in the measurement gas between two levels, one of which does not allow reduction of NOx while the other allows the NOx reduction.

Referring to FIG. 25 showing the principle of the known methods as described above, a first and a second sensing element 61, 62, which are formed independently of each other, have respective internal spaces 65, 66 which communicate with an exterior measurement-gas space through corresponding diffusion resistance portions 63, 64, and respective electrochemical pumping cells 67, 68 using solid electrolyte. The first sensing element 61 effects pumping of only oxygen under a predetermined diffusion resistance, and the oxygen concentration is obtained by multiplying the pumping current $Ip_1$ by a current sensitivity coefficient $K_1$. The second sensing element 62 having an electrode or catalyst capable of reducing NOx effects pumping of both oxygen and NOx under a predetermined diffusion resistance, and a sum of the oxygen and NOx concentrations is obtained by multiplying the pumping current $Ip_2$ by a current sensitivity coefficient $K_2$. Thus, the NOx concentration "Cn" is calculated according to the following equation:

$$Cn = K_2 \cdot Ip_2 - K_1 \cdot Ip_1$$

In the above method of measuring NOx, however, a considerably small current flows due to NOx whose concentration is measured, and a considerably large portion of the limiting current is caused by a large amount of oxygen contained in the measurement gas. Therefore, the small current value corresponding to NOx is obtained from a difference between the two large pumping currents $Ip_1$, $Ip_2$. Where the method uses only one sensor in which the oxygen partial pressure is regulated as described above, the NOx cannot be continuously measured, and the operating response and measuring accuracy are deteriorated. Where the method uses two sensors having different oxygen partial pressures, a measurement error is likely to occur with a great change in the oxygen concentration of the measurement gas, and therefore this method cannot be employed in automobile applications, for example, where the oxygen concentration in exhaust gases varies to a large extent. This is because the dependency of the pumping current of one of the sensors on the oxygen concentration differs from that of the other sensor. In the case of an automobile running under the air/fuel ratio of 20, for example, the oxygen concentration is generally several percentages of exhaust gases, whereas the NOx concentration is several hundreds of ppm, which is about 1/100 of the oxygen. If the dependency of the pumping current on the oxygen concentration slightly differs between the two sensors, therefore, a difference in the limiting currents due to the varying oxygen concentration becomes larger than a change in the limiting currents due to NOx whose concentration is measured. The known method involves other problems. That is, if diffusion means or small leak formed in the pumping cell is clogged with oil ash in the exhaust gases, the pumping current may be undesirably changed, resulting in reduced measuring accuracy. With a great variation in the temperature of the exhaust gases, the measurement results may involve some abnormality. Further, a difference in the chronological changes in the characteristics between the two sensors may lead to measuring errors, making the sensors undurable for use for a long period of time.

While the oxygen present in the measurement gas causes various problems upon measurement of NOx, as described above, the oxygen also causes similar problems, such as reduced measuring accuracy, upon measurement of gas components other than NOx, and there has been a strong need to solve these problems.

SUMMARY OF THE INVENTION

It is therefore a first object of the present invention to provide a method for measuring the concentration of a desired component in a measurement gas, in particular, a gas component containing bonded oxygen, without being affected by the oxygen concentration or its variation, thus assuring improved operating response even in repeated measurements, and improved measuring accuracy for a long period of time. It is a second object of the invention to provide a sensing device adapted for measuring the concentration of a gas component according to the above method. The present invention may be practiced for an NOx sensor which is able to measure an increased range of NOx, in combustion gases produced under a wide range of the air/fuel ratio, that is, from a rich-burn combustion gas produced by combustion of a fuel-rich air-fuel mixture to a lean-burn combustion gas produced by combustion of a fuel-lean air-fuel mixture.

The first object may be accomplished according to a first aspect of the present invention, which provides a method of measuring a concentration of a gas component of a measurement gas, comprising the steps of: introducing the measurement gas containing the gas component, from an external measurement-gas space into a first internal space, under a first diffusion resistance; controlling an amount of oxygen in the measurement gas within the first internal space, so as to produce an atmosphere which does not substantially affect measurement of the gas component and which does not convert the gas component; introducing the atmosphere from the first internal space into a second internal space, under a second diffusion resistance; and measuring the concentration of the gas component present in the atmosphere in the second internal space.

According to the above-described method of measuring a desired gas component of a measurement gas, the concentration of the gas component can be measured with high accuracy, without being affected by the oxygen concentration or its variation in the measurement gas, assuring improved operating response even in repeated measurements, and improved measuring accuracy for a long period of time. Further, the present method enables measurement of an increased range of NOx, in combustion gases produced under a wide range of the air/fuel ratio, that is, from a rich burn region using excessive fuel to a lean burn region using excessive air, without being affected by oil ash.

In one advantageous feature of the first aspect of the invention as described above, the amount of oxygen in the measurement gas is controlled in the first internal space so that the atmosphere has a substantially negligible concentration level of oxygen.

In another advantageous feature of the same aspect of the invention, the amount of oxygen in the measurement gas is controlled in the first internal space by an oxygen pumping action of an electrochemical cell.

The above first object may also be accomplished by a second aspect of the present invention, which provides a method of measuring a concentration of a gas component of a measurement gas, the gas component having bonded oxygen, comprising the steps of: introducing the measurement gas containing the gas component having bonded oxygen, from an external measurement-gas space into a first internal space, under a first diffusion resistance; controlling an amount of oxygen in the measurement gas within the first internal space, so as to produce an atmosphere which does not substantially affect measurement of the gas component and which does not substantially reduce or decompose the gas component; introducing the atmosphere from the first internal space into a second internal space, under a second diffusion resistance; reducing or decomposing the gas component present in the atmosphere in the second internal space, and pumping out oxygen produced upon the reduction or decomposition, by an oxygen pumping action of an electrochemical cell; and detecting a pumping current flowing through the electrochemical cell, so as to calculate the concentration of the gas component in the measurement gas, on the basis of the pumping current.

In one advantageous feature of the second aspect of the invention, the amount of oxygen in the measurement gas is controlled in the first internal space so that the atmosphere has a substantially negligible level of an oxygen concentration.

In another advantageous feature of the same aspect of the invention, the amount of oxygen in the measurement gas is controlled in the first internal space by an oxygen pumping action of an electrochemical cell.

The above-indicated first object may also be attained according to a third aspect of the present invention, which provides a method of measuring a concentration of a gas component of a measurement gas, the gas component having bonded oxygen, comprising the steps of: introducing the measurement gas containing the gas component having bonded oxygen, from an external measurement-gas space into a first internal space, under a first diffusion resistance; regulating an oxygen partial pressure in the first internal space, by an oxygen pumping action of a first electrochemical cell, so as produce an atmosphere having a predetermined level of the oxygen partial pressure, which does not cause reduction or decomposition of the gas component at a first elevated temperature of the first internal space; introducing the atmosphere from the first internal space into a second internal space, under a second diffusion resistance; regulating an oxygen partial pressure in the second internal space, by pumping out oxygen due to an oxygen pumping action of a second electrochemical cell, so that the oxygen partial pressure is regulated to a predetermined level which allows reduction or decomposition of the gas component at a second elevated temperature of the second internal space, the second electrochemical cell further pumping out oxygen produced upon reduction or decomposition of the gas component; and detecting a pumping current flowing through the second electrochemical cell, so as to calculate the concentration of the gas component in the measurement gas, on the basis of the pumping current.

The second internal space may be filled with a porous body having the second diffusion resistance.

In one advantageous feature of the third aspect of the invention, the oxygen partial pressure in the first internal space is detected, and the oxygen pumping action of the first electrochemical cell is controlled by varying a voltage applied to the first electrochemical cell, based on the detected oxygen partial pressure, so that the oxygen partial pressure in the first internal space is regulated to a constant value.

In another advantageous feature of the same aspect of the invention, the oxygen pumping action of the second electrochemical cell is effected by applying thereto a constant voltage which provides a diffusion limiting current to the gas component, the oxygen partial pressure of the atmosphere in the second internal space being regulated by application of the diffusion limiting current.

In a further advantageous feature of the same aspect of the invention, the second elevated temperature of the second internal space is not lower than the first elevated temperature of the first internal space.

In a still further advantageous feature of the same aspect of the invention, the oxygen partial pressure in the second internal space is not higher than the oxygen partial pressure in the first internal space.

The above-indicated gas component having bonded oxygen, which is to be measured by the present method, may be advantageously selected from among NOx, $CO_2$, and $H_2O$.

The above-indicated second object may be attained according to a fourth aspect of the present invention, which provides a sensing device for measuring a concentration of a gas component of a measurement gas, the gas component having bonded oxygen, comprising: means for defining a first internal space which communicates with an external measurement-gas space where the measurement gas is present; first diffusion means for introducing the measurement gas containing the gas component from the external measurement-gas space into the first internal space, under a first diffusion resistance; first oxygen pumping means comprising an electrochemical cell having a first oxygen-ion conductive solid electrolyte and a pair of electrodes formed thereon, for effecting an oxygen pumping action with respect to the first internal space, so that an oxygen partial pressure of an atmosphere in the first internal space is regulated to a predetermined level which does not substantially permit reduction or decomposition of the gas component; means for defining a second internal space which communicates with the first internal space; second diffusion means for introducing the atmosphere from the first internal space into the second internal space, under a second diffusion resistance; second oxygen pumping means comprising an electrochemical cell having a second oxygen-ion conductive solid electrolyte and a pair of electrodes formed thereon, for pumping out oxygen from an atmosphere in the second internal space, so that an oxygen partial pressure of the atmosphere in the second internal space is regulated to a predetermined value which permits reduction or decomposition of the gas component, whereby the gas component present in the atmosphere in the second internal space is reduced or decomposed, the second oxygen pumping means further pumping out oxygen produced upon the reduction or decomposition; and current detecting means for detecting a pumping current flowing through the second oxygen pumping means.

The above-described sensing device yields the same effects or advantages as provided by the method of the present invention.

In one preferred form of the fourth aspect of the invention, the sensing device further includes a catalyst disposed in the second internal space, for reducing or decomposing the gas component so as to detach oxygen from the gas component.

In the above form of the invention, one of the pair of electrodes of the electrochemical cell of the second oxygen pumping means, which is disposed in the second internal space, may serve as the catalyst.

In another preferred form of the same aspect of the invention, the sensing device has a sensing element which includes the first and second oxygen-ion conductive solid electrolytes as integral parts thereof, the first and second internal spaces, the first and second diffusion means and the first and second oxygen pumping means being formed in the sensing element.

In the above form of the invention, the sensing element may have a narrow, flat space having a predetermined diffusion resistance, which space has an opening exposed to the external measurement-gas space, the flat space comprising the first and second diffusion means, the first internal space consisting of a first portion of the flat space adjacent to the opening, in which the first oxygen pumping means is provided, the second internal space consisting of a second portion of the flat space remote from the opening and inside of the first portion, in which the second oxygen pumping means is provided.

Further, the first and second oxygen-ion conductive solid electrolytes may form an oxygen-ion conductive solid electrolyte layer, or two separate oxygen-ion conductive solid electrolyte layers.

The sensing device as described above may further include a porous body filling the opening of the flat space of the sensing element, the porous body having a predetermined diffusion resistance.

In a further preferred form of the invention, the sensing device further includes a heater for heating the first and second internal spaces to respective predetermined temperatures. In this case, the sensing device can effectively operates even at a relatively low temperature, while effectively decomposing the gas component of the measurement gas.

The above-indicated second object may also be attained according to a fifth aspect of the present invention, which provides a sensing device for measuring an amount (concentration) of a gas component of a measurement gas, comprising a sensing element including an oxygen-ion conductive solid electrolyte as an integral part thereof, the gas component having bonded oxygen, the sensing element comprises: means for defining a first internal space which communicates with an external measurement-gas space where the measurement gas is present; first diffusion means for introducing the measurement gas containing the gas component from the external measurement-gas space into the first internal space, under a first diffusion resistance; means for defining a second internal space communicating with the first internal space; a catalyst disposed in the second internal space; second diffusion means for introducing an atmosphere in the first internal space into the second internal space, under a second diffusion resistance; a heater for heating the first and second internal spaces up to first and second temperatures, respectively; first oxygen pumping means comprising an electrochemical cell having the oxygen-ion conductive solid electrolyte and a pair of electrodes formed thereon, for effecting an oxygen pumping action with respect to the first internal space, so that an oxygen partial pressure of the atmosphere in the first internal space is regulated to a predetermined level which does not substantially allow reduction or decomposition of the gas component at the first temperature; second oxygen pumping means comprising an electrochemical cell having the oxygen-ion conductive solid electrolyte and a pair of electrodes formed thereon, for pumping out oxygen from an atmosphere in the second internal space, so that an oxygen partial pressure of the atmosphere in the second internal space is regulated to a predetermined value which allows reduction or decomposition of the gas component at the second temperature, whereby the gas component present in the atmosphere in the second internal space is reduced or decomposed, the second oxygen pumping means further pumping out oxygen produced upon the reduction or decomposition; and current detecting means for detecting a pumping current flowing through the second oxygen pumping means.

The second internal space may be formed separately from the first internal space within the sensing element. In other cases, the second diffusion means may consist of a porous body having the second diffusion resistance, the second internal space being filled with the porous body.

In one preferred form of the fifth aspect of the present invention, the sensing device further includes oxygen partial pressure detecting means for detecting the oxygen partial pressure of the atmosphere in the first internal space, the first oxygen pumping means applying a controlled current to the pair of electrodes of the electrochemical cell of the first pumping means, on the basis of the oxygen partial pressure detected by the detecting means, so as to regulate the oxygen partial pressure in the first internal space, with improved accuracy and ease.

In another preferred form of the same aspect of the invention, a reference-gas chamber containing a reference gas is formed in the sensing element, separately from the first and second internal spaces, the oxygen partial pressure detecting means comprising an electrochemical cell which comprises an oxygen-ion conductive solid electrolyte extending between the reference-gas chamber and the first internal space, a reference electrode located in the reference-gas chamber and formed in contact with the solid electrolyte, and a measuring electrode located in the first internal space and formed in contact with the solid electrolyte. In this case, the reference-gas chamber is preferably exposed at an opening thereof to an ambient atmosphere, such that the ambient atmosphere is introduced into the reference-gas chamber through the opening, to provide the reference gas.

In the above form of the invention, the electrochemical cell of the second oxygen pumping means may comprise an oxygen-ion conductive solid electrolyte extending between the second internal space and the reference-gas chamber, a first pumping electrode located in the second internal space and formed in contact with the solid electrolyte, and a second pumping electrode located in the reference-gas chamber and formed in contact with the solid electrolyte. Preferably, the oxygen-ion conductive solid electrolyte of the electrochemical cell of the second oxygen pumping means and the oxygen-ion conductive solid electrolyte of the electrochemical cell of the oxygen partial pressure detecting means constitute an integral oxygen-ion conductive solid electrolyte, and the second pumping electrode and the reference electrode formed on the solid electrolyte constitute a common electrode.

In the above form of the invention, the first pumping electrode of the electrochemical cell of the second oxygen pumping means, which is disposed in the second internal space, may also serve as the catalyst. This leads to a simplified process of manufacturing the device.

The above-indicated first pumping electrode may be formed of a porous cermet consisting of a ceramic, and a metal which is able to reduce or decompose the gas component having bonded oxygen.

Further, the catalyst may be disposed in the second internal space, in the vicinity of the first pumping electrode of the electrochemical cell of the second oxygen pumping means, or may be superposed on the first pumping electrode of the electrochemical cell of the second oxygen pumping means.

The above-indicated heater may be located nearer to the second internal space than to the first internal space within the sensing element, so that the second internal space is heated to a higher temperature than the first internal space. With the heater thus located, the gas component can be more easily reduced or decomposed in the second internal space.

The above-indicated second diffusion resistance of the second diffusion means is preferably determined to be larger than the first diffusion resistance of the first diffusion means. This effectively eliminates an adverse influence on the measurement of the gas component of the measurement gas, due to clogging by oil ash.

The gas component having bonded oxygen, which is to be measured by the present sensing device, may be selected from among NOx, $CO_2$, and $H_2O$.

The second object indicated above may also be achieved according to a fifth aspect of the present invention, which provides a sensing device for measuring a concentration of a gas component of a measurement gas, the gas component having bonded oxygen, comprising: (a) means for defining a first internal space which communicates with an external measurement-gas space where the measurement gas is present; (b) first diffusion means for introducing the measurement gas containing the gas component from the external measurement-gas space into the first internal space, under a first diffusion resistance; (c) first oxygen pumping means comprising an electrochemical cell having a first oxygen-ion conductive solid electrolyte and a pair of electrodes formed thereon, for effecting an oxygen pumping action with respect to the first internal space, so that an oxygen partial pressure of an atmosphere in the first internal space is regulated to a predetermined level which does not substantially allow reduction or decomposition of the gas component; (d) means for defining a second internal space which communicates with the first internal space; (e) second diffusion means for introducing the atmosphere from the first internal space into the second internal space, under a second diffusion resistance; (f) second oxygen pumping means comprising an electrochemical cell having a second oxygen-ion conductive solid electrolyte and a pair of electrodes formed thereon, for pumping out oxygen from an atmosphere in the second internal space, so that an oxygen partial pressure of the atmosphere in the second internal space is regulated to a predetermined value which allows reduction or decomposition of the gas component, whereby the gas component present in the atmosphere in the second internal space is reduced or decomposed, the second oxygen pumping means further pumping out oxygen produced upon the reduction or decomposition; and (g) current detecting means for detecting a pumping current flowing through the second oxygen pumping means, and wherein at least one of electrodes exposed to the first and second internal spaces includes an alloy consisting of Au and the balance consisting principally of an element selected from the platinum group.

The above-indicated alloy preferably comprises 0.01–36 wt. % of Au.

Preferably, the above-indicated alloy is used for the electrode or electrodes exposed to the first internal space, for example, for the inner pumping electrode of the electrochemical cell of the first oxygen pumping means, and for a measuring electrode of oxygen partial pressure detecting means provided for detecting the oxygen partial pressure of the atmosphere in the first internal space as described above. Where these inner pumping electrode and measuring electrode are formed of a material including the alloy containing Au and the platinum group element such as Pt, Rh or Pd, these electrodes in the first internal space have reduced ability or activity of reducing the NOx component, so that the amount of oxygen to be introduced from the first internal space into the second internal space is minimized, whereby the accuracy of determination of the NOx component is accordingly improved.

However, the alloy may be used for the electrode or electrodes in the second internal space, for example, the inner pumping electrode of the electrochemical cell of the second oxygen pumping means, and for an electrode of auxiliary oxygen pumping means provided for pumping out oxygen from said second internal space in cooperation with said second oxygen pumping means. Where the alloy is used for the inner pumping electrode of the second oxygen pumping means, a catalyst should be provided in the second internal space. For instance, the catalyst layer is formed so as to cover the inner pumping electrode or disposed separately from and in the vicinity of the inner pumping electrode, as described above. Further, a heater is desirably provided to heat the first and second internal spaces so as to prevent the reduction of the NOx component in the first internal space and promote the reduction in the second internal space.

For reducing or minimizing the NOx reducing ability of the electrode or electrodes within the first internal space, in particular, the Au content of the alloy should be 0.01 wt. % or larger and preferably 0.03 wt. % or larger. On the other hand, the Au content of the alloy should be 36. % or smaller, to prevent abnormal growth of grains of the alloy, which makes it difficult to co-fire a green paste of the electrode material including the Au alloy with green sheets for the solid electrolyte layers, at a sufficiently high temperature higher than 1300° C.

For increased durability of the Au-alloy electrode or electrodes and sensing element, the Au content of the alloy is desirably 1.0 wt. % or smaller. To avoid functional deterioration of the Au-alloy electrode or electrodes, the Au content is desirably not larger than 0.8 wt. %.

BRIEF DESCRIPTION OF THE DRAWINGS

The above and optional objects, features and advantages of the present invention will be better understood by reading the following detailed description of its presently preferred embodiments, when considered in conjunction with the accompanying drawings, in which.

DETAILED DESCRIPTION OF THE PREFERRED EMBODIMENTS

Figure 1:
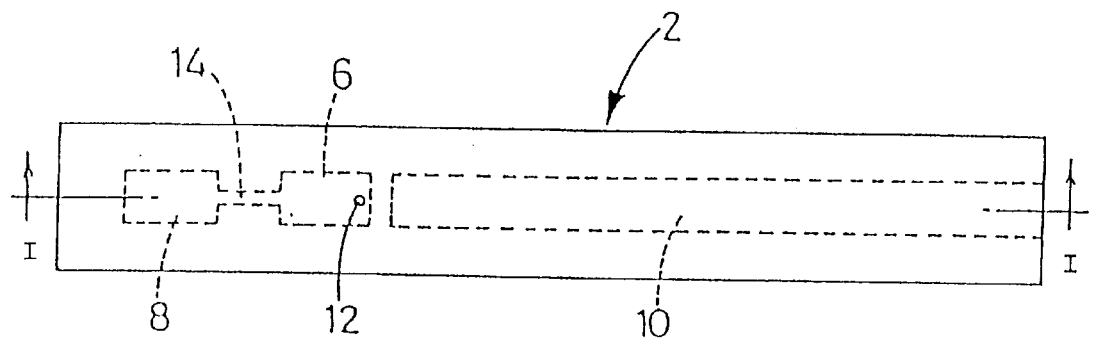
FIG. 1 is a plane view showing a sensing element of an NOx sensor as one embodiment of the present invention.
Figure 2:
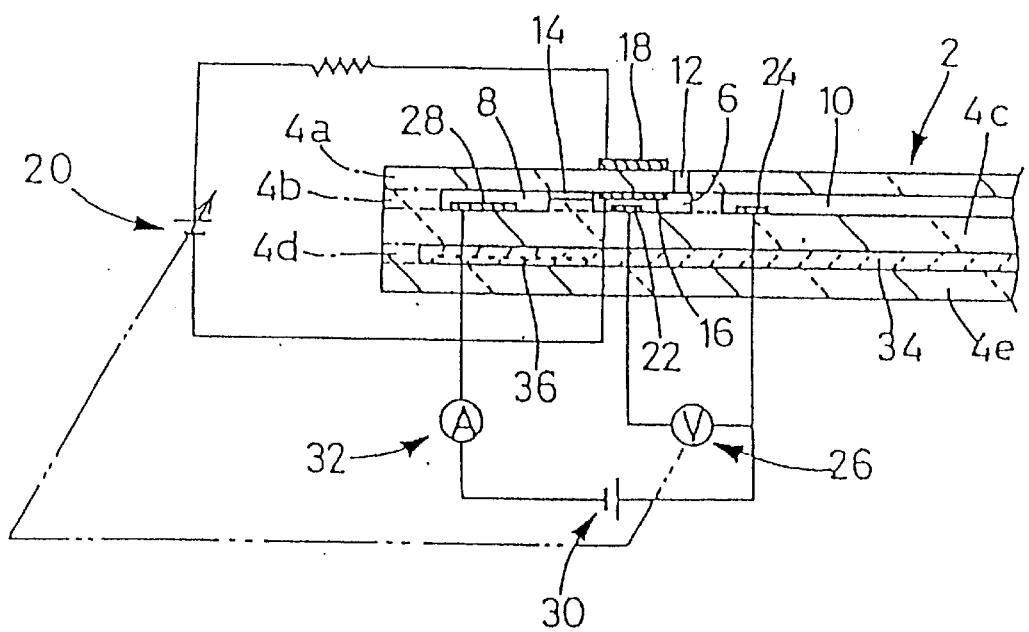
FIG. 2 is an elevational view in cross section taken along line A—A of FIG. 1, which shows in enlargement a principal part of the sensing element of FIG. 1.

Referring first to FIGS. 1 and 2, there is illustrated an NOx sensor as one preferred embodiment of a sensing device of the present invention, which is adapted to determine the concentration of NOx as a component contained in a measurement gas, according to a method of the present invention.

In FIGS. 1 and 2, reference numeral 2 denotes an elongate, planar sensing element having a relatively large length. This sensing element 2 has an integral laminar structure including a plurality of highly dense, gastight oxygen-ion conductive solid electrolyte layers 4a, 4b, 4c, 4d, 4e which are superposed on each other, as shown in FIG. 2. Each of the solid electrolyte layers 4a–4e is formed of a known oxygen-ion conductive solid electrolyte material, such as zirconia. The thus integrally formed sensing element 2 is produced by firing unfired solid electrolyte layers into an integral laminar structure or body, as known in the art.

In the integral sensing element 2, a first internal space 6 and a second internal space 8 are separately formed such that the second internal space 8 is located nearer to the distal end of the sensing element 2. Each internal space 6, 8 has a narrow and flat rectangular shape as seen in a plane parallel to opposite major surfaces of the element 2. Independently of the first and second internal spaces 6, 8, a reference-gas channel 10 serving as a reference-gas chamber is formed so as to extend in the longitudinal direction of the sensing element 2, such that the channel 10 is open at the proximal end of the element 2, for communication with the ambient atmosphere. In the instant embodiment, the first and second internal spaces 6, 8 and reference-gas channel 10 are formed in substantial the same plane, by closing respective apertures formed through the solid electrolyte layer 4b, with the upper and lower solid electrolyte layers 4a, 4c. The sensing element 2 further has a first diffusion controlling passage 12 as a first diffusion means, which is formed through the thickness of the upper solid electrolyte layer 4a. The first diffusion controlling passage 12 communicates the first internal space 6 with an external measurement-gas space where a measurement gas to be measured by the NOx sensor is present, so that the measurement gas is introduced into the first internal space 6 through the passage 12, under a predetermined diffusion resistance provided by the passage 12. Further, second diffusion means in the form of a second diffusion controlling passage 14 is formed in the solid electrolyte layer 4b, to extend between the first and second internal spaces 6, 8. This second diffusion controlling passage 14 communicates with the first and second internal spaces 6, 8, so that the atmosphere in the first internal space 6 is introduced into the second internal space 8 through the passage 14, under a predetermined diffusion resistance provided by the passage 14.

Inner electrode (pumping electrode) 16, which is a rectangular porous platinum electrode, is formed on the inner surface of the solid electrolyte layer 4a which is exposed to the first internal space 6. Further, outer electrode (pumping electrode) 18, which is also a rectangular porous platinum electrode, is formed on the outer surface of the solid electrolyte layer 4a, such that the inner and outer electrodes 16, 18 are aligned with each other in a plane parallel to the major surfaces of the sensing element 2. These electrodes 16, 18 and solid electrolyte layer 4a constitute an electrochemical cell of first oxygen pumping means, that is, a first electrochemical pumping cell. In operation, a desired voltage is applied between the inner and outer electrodes 16, 18 of the first electrochemical pumping cell, by means of an external variable-voltage power supply 20, to generate a current flow in a predetermined direction, so that oxygen in the atmosphere in the first internal space 6 is pumped out into the external measurement-gas space, or oxygen is pumped from the external measurement-gas space into the first internal space 6. In this embodiment, each of the porous platinum electrodes 16, 18 consists of a cermet electrode formed of a mixture of platinum and zirconia ($ZrO_2$).

Measuring electrode 22, which is a rectangular, porous platinum electrode, is formed on the surface of the solid electrolyte layer 4c which is exposed to the first internal space 6, while reference electrode 24, which is a similar porous platinum electrode, is formed on the surface of the solid electrolyte layer 4c which is exposed to the the reference-gas channel 10. These measuring electrode 22, reference electrode 24 and solid electrolyte layer 4c constitute an electrochemical cell of oxygen partial pressure detecting means, that is, an electrochemical sensing cell. As known in the art, an electromotive force (EMF) is induced between the measuring electrode 22 and the reference electrode 24, based an a difference in the oxygen concentration between the atmosphere in the first internal space 6 and the reference gas in the reference-gas channel 10. This electromotive force is measured by a potentiometer 26, to thus detect the oxygen partial pressure in the atmosphere in the first internal space 6. Then, a voltage of the variable power supply 20 is regulated or controlled, on the basis of the level of the oxygen partial pressure as detected by the potentiometer 26, whereby the oxygen partial pressure in the atmosphere in the first internal space 6 is kept at a constant level.

Internal pumping electrode (first pumping electrode) 28 is formed on the surface of the solid electrolyte layer 4c, such that the electrode 28 is located within the second internal space 8. This internal pumping electrode 28 is formed of porous cermet consisting of rhodium (Rh) as a metal capable of reducing NOx, and zirconia as a ceramic material. Thus, the electrode 28 also functions as an NOx reduction catalyst which is able to reduce NOx present in the atmosphere in the second internal space 8. When a constant voltage is applied between the internal pumping electrode 28 and the reference electrode (second pumping electrode) 24 disposed in the reference-gas channel 10, by means of a power supply 30, oxygen in the atmosphere within the second internal space 8 is pumped out into the reference-gas channel 10. Thus, the reference electrode 24 also functions as a pumping electrode, and cooperates with the internal pumping electrode 28 and solid electrolyte layer 4c to constitute an electrochemical cell of second oxygen pumping means, that is, a second electrochemical pumping cell. Ammeter 32 is provided to detect a pumping current which flows by the pumping action of the second oxygen pumping means. The constant voltage applied by the power supply 30 is determined so as to provide a limiting current that enables the second electrochemical pumping cell to effect the pumping of the oxygen generated by reduction of NOx, which is introduced into the second internal space 28, under the diffusion resistance provided by the second diffusion resistance channel 14.

The sensing element 2 also incorporates an alumina insulating layer 34 which is laminated integrally on the solid electrolyte layers 4c, 4e, such that the layer 34 is surrounded by three solid electrolyte layers 4c, 4e and 4d. Heater 36 is embedded within the alumina insulating layer 34, and is operated by an external power supply. As shown in FIG. 2, the heater 36 is located in a distal end portion of the sensing element 2 in which the second internal space 8 is formed, so that the second internal space 8 is heated to a higher temperature than the first internal space 6, in other words, the internal pumping electrode 28 is heated to a higher temperature than the inner electrode 16 and measuring electrode 22. For example, the heater 36 is located so that the inner electrode 16 and measuring electrode 22 in the first internal space 6 is heated up to 400° C.–600° C. while the internal pumping electrode 28 in the second internal space 8 is heated up to 700° C.–900° C., as the temperature of the measurement gas varies in the range from 300° C. to 850° C.

The thus constructed sensing element 2 is positioned at its distal end portion within the external measurement-gas space. Thus, the measurement gas is introduced into the first internal space 6, through the first diffusion controlling passage 12, under a predetermined diffusion resistance. Then, the measurement gas in the first internal space 6 is subjected to the oxygen pumping action in which a suitable voltage is applied between the inner and outer electrodes 16, 18 of the first electrochemical pumping cell, so that the oxygen partial pressure in the first internal space 6 is controlled to a predetermined level, for example, $10^{-6}$ atm.

To keep the oxygen partial pressure in the atmosphere in the first internal space 6 at the predetermined constant level, a voltage applied between the two electrodes 16, 18 of the first electrochemical pumping cell by the variable power supply 20 is regulated so that the electromotive force induced between the measuring electrode 22 and the reference electrode 24 of the electrochemical sensing cell, which is detected by the potentiometer 26, is equal to 203 mV at 500° C., for example, according to the Nernst equation known in the art. In this manner, the oxygen partial pressure in the first internal space 6 can be easily controlled to $10^{-6}$ atm as desired. That is, the voltage applied to the first electrochemical pumping cell is regulated so that the above-described electromotive force corresponds to a difference between a desired oxygen concentration in the first internal space 6 and the oxygen concentration of the reference gas. It is to be noted that the first diffusion controlling passage 12 functions to reduce an amount of oxygen in the measurement gas diffusing into the first internal space 6, and thus restrict a current flowing through the first electrochemical pumping cell, upon application of a voltage to the pumping cell.

In the first internal space 6, the oxygen partial pressure is controlled so that NOx contained in the atmosphere is not reduced by the inner electrode 16 and the measuring electrode 22, that is, the reaction: $NO \rightarrow 1/2N_2 + 1/2O_2$, for example, does not take place, even at a high temperature elevated by the external measurement gas and the heater 36. If NOx in the atmosphere is reduced in the first internal space 6, NOx cannot be accurately measured in the second internal space 8, as described later. In this sense, it is necessary to establish appropriate conditions or environment in the first internal space 6 so that NOx is not reduced by a component (at least a component of the inner electrode 16 of the first electrochemical pumping cell), which might otherwise be involved in reduction of NOx in the first internal space 6.

The measurement gas, whose oxygen partial pressure has been controlled in the first internal space 6 in the above manner, is then introduced into the second internal space 8, through the second diffusion controlling passage. 14, under a predetermined diffusion resistance. Then, the measurement gas in the second internal space 8 is subjected to an oxygen pumping action, in which a predetermined or constant voltage, e.g., 449 mV, is applied at 700° C. between the internal pumping electrode 28 and the reference electrode 24 of the second electrochemical pumping cell, so that oxygen is pumped from the second internal space 8 into the reference-gas channel 10. As a result, the oxygen concentration is reduced down to $10^{-10}$ atm in the second internal space 8, particularly at the three phase boundary of the internal pumping electrode 28. Consequently, NOx is reduced, that is, the reaction: $NO \rightarrow 1/2N_2 + 1/2O_2$, for example, takes place, around the internal pumping electrode 28 serving as NOx reduction catalyst. At this time, the current flowing through the second electrochemical pumping cell is proportional to the oxygen concentration of the atmosphere in the second internal space 8, that is, a sum of the oxygen concentration of the atmosphere in the first internal space 6 and the concentration of oxygen generated by reduction of NOx at the internal pumping electrode 28. Since the oxygen concentration of the atmosphere in the first internal space 6 is kept constant, as described above, the current flowing through the second electrochemical pumping cell is proportional to the concentration of NOx. The NOx concentration corresponds to an amount of NOx which is diffused under the resistance of the second diffusion controlling passage 14. In this manner, the measurement of the NOx concentration can be effected.

When the oxygen concentration of the atmosphere in the first internal space 6 is equal to 0.02 ppm while the NO concentration of the measurement gas is equal to 100 ppm, for example, the current flowing through the second electrochemical pumping cell corresponds to 50.02 ppm, that is, a sum of the concentration of oxygen (50 ppm) generated by reduction of NO and the oxygen concentration (0.02 ppm) of the atmosphere in the first internal space 6. Thus, the pumping current value of the second electrochemical pumping cell substantially represents the amount of NO reduced, and does not depend much on the oxygen concentration of the measurement gas.

Figure 24:
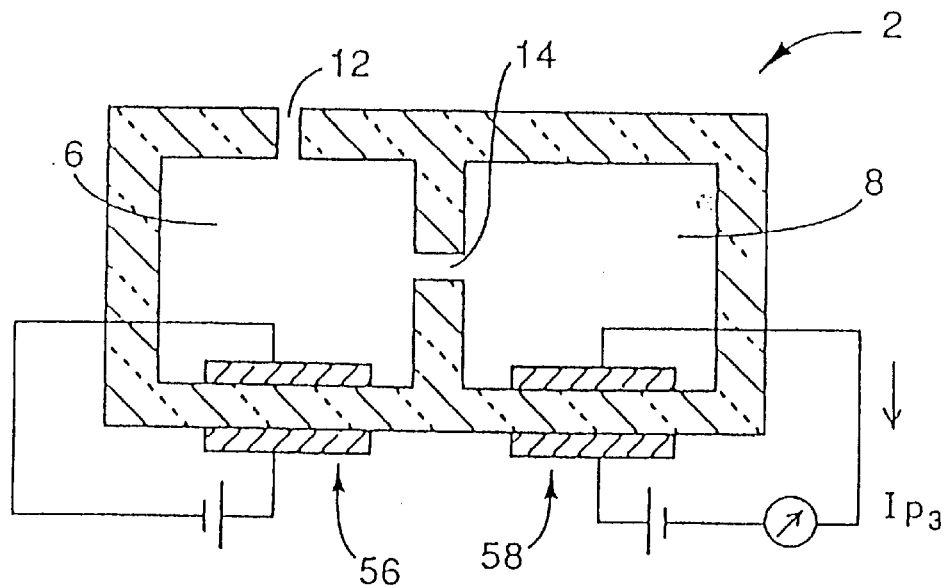
FIG. 24 is a cross sectional view of a sensing element, for explaining the principle of the present invention.

The principle of the present invention will be described in detail, referring to FIG. 24. In this figure, the measurement gas is introduced into the first internal space 6, through the first diffusion controlling passage 12, and the oxygen partial pressure in the first internal space 6 is regulated to a predetermined, desirably low level, by the pumping action of the first electrochemical pumping cell 56 serving as oxygen concentration control means. NOx is not reduced in this first internal space 6. Then, the atmosphere in the first internal space 6, having the thus regulated oxygen pressure, is introduced, through the second diffusion controlling passage 14, into the second internal space 8 where NOx is reduced. The oxygen generated by reduction of NOx is then pumped out from the second internal space 8, by means of the second electrochemical pumping cell 58, and the amount of NOx in the measurement gas is measured on the basis of a magnitude of a current flowing through the second electrochemical cell 58.

In the above-described method, the NOx concentration "Cn" is obtained according to an equation: $Cn = K \cdot Ip_3 - A$, where K is a current sensitivity coefficient, $Ip_3$ is a current flowing through the second electrochemical pumping cell 58, and A is a constant indicative of a small amount of oxygen remaining in the first internal space 6. It will be understood that the most part of $Ip_3$ depends on the oxygen generated by decomposition of the NOx component contained in the measurement gas, and that the present method permits highly accurate measurement of even a slight amount of NOx, without being affected by oxygen in the measurement gas, as compared with conventional methods. The outer electrodes of the first and second electrochemical pumping cells 56, 58, which are not exposed to the internal spaces 6, 8, may be located anywhere provided that oxygen can be discharged from these electrodes. For example, the outer electrodes are located in the ambient air.

Figure 3:
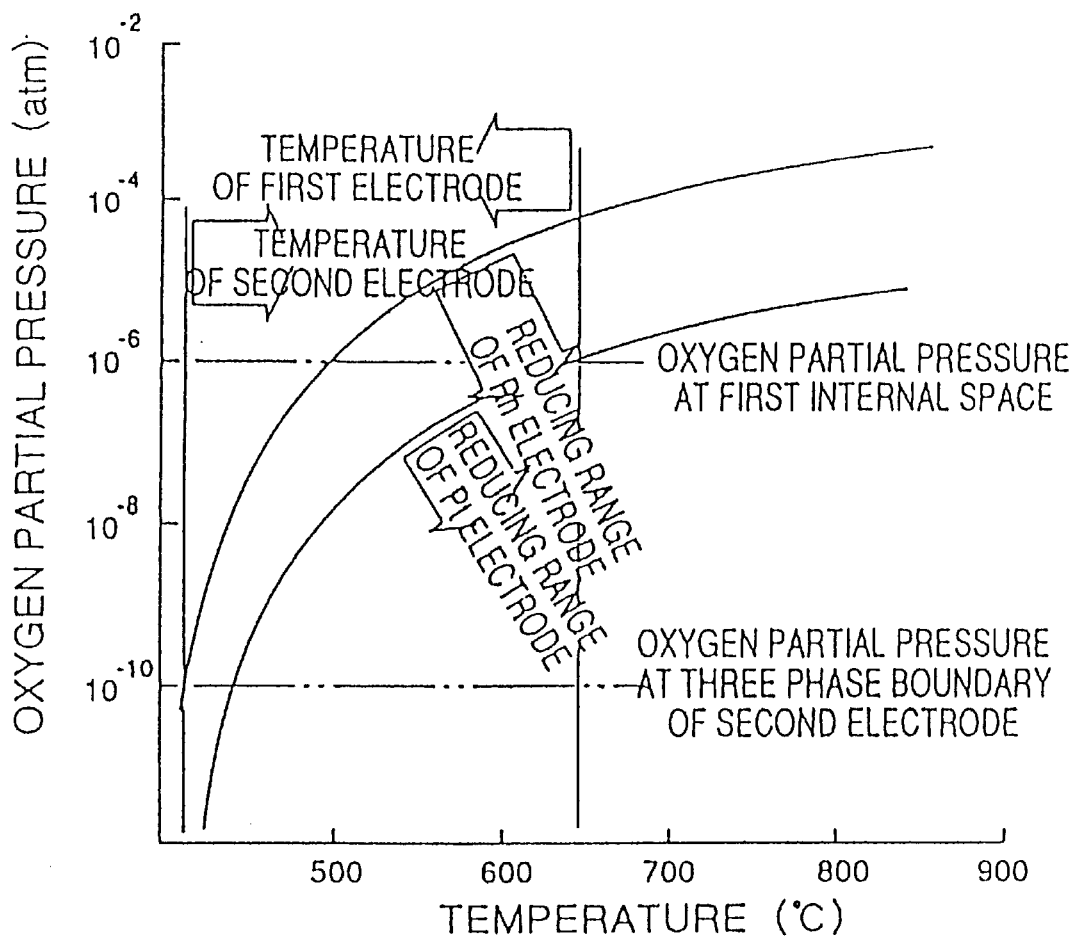
FIG. 3 is a graph showing a first method of controlling the temperatures of electrodes and the oxygen partial pressures in first and second internal spaces.

The graph of FIG. 3 shows one example of the relationship between the temperatures at the electrodes in the respective internal spaces 6, 8 and the oxygen partial pressures in these internal spaces 6, 8 which are controlled in the manner as described above. In this graph, the first electrode is a cermet Pt electrode containing $ZrO_2$ and Pt in the volume ratio of 40:60, which electrode is co-fired with a $ZrO_2$ substrate at 1400° C., while the second electrode is a cermet Rh electrode containing $ZrO_2$ and Rh in the volume ratio of 40:60. This graph also shows the capability of these electrodes to reduce NO in relation to the oxygen partial pressure and the temperature at each internal space. It will be apparent from FIG. 3 that the Pt electrode is only capable of reducing NO at a relatively high temperature, under a relatively low oxygen partial pressure, while the Rh electrode is capable of reducing NO at a relatively low temperature, under a relatively high oxygen partial pressure.

It will be understood from the above-indicated relationship between the oxygen concentration and the temperature that the temperature of the first electrodes, that is, the Pt electrodes (inner electrode 16 and measuring electrode 22) disposed in the first internal space 6, is controlled to within a range in which NO is not reduced by the first electrodes. For example, when the oxygen partial pressure in the first internal space 6 is set to $10^{-6}$ atm, as shown in FIG. 3, the location and power of the heater 36 are determined so that the temperature in the first internal space 8 is equal to or lower than 650° C., even when the temperature of the measurement gas is 900° C. (which is approximately the maximum temperature of the exhaust gases of automobiles). The measurement gas whose oxygen partial pressure is controlled to $10^{-6}$ atm in the first internal space 6 is then introduced, through the second diffusion controlling passage 14, into the second internal space 8 where a voltage of 450 mV is applied to the internal pumping electrode 28 and the reference electrode 24, to pump out oxygen from the second internal space 8 into the reference-gas channel 10. Thus, the oxygen partial pressure at the three phase boundary of the internal pumping electrode 28 is lowered to about $10^{-10}$ atm (which corresponds to the electromotive force of 450 mV that develops across the internal pumping electrode 28 and the reference electrode 24). It will be noted from FIG. 3 that the second electrode, that is, the Rh electrode as the internal pumping electrode 28, is capable of reducing NO at 410° C. or higher, under the oxygen partial pressure of $10^{-10}$ atm. Accordingly, the location and power of the heater 36 are determined so that the temperature of the internal pumping electrode 28 (or second electrode) disposed in the second internal space 8 is equal to or higher than 410° C., even when the temperature of the measurement gas is 300° C. (which is approximately the lowest temperature of the automobile exhaust gases). In this manner, NO is reduced at the three phase boundary of the internal pumping electrode 28 as the second electrode, to generate oxygen which causes a current to flow through the second electrochemical pumping cell. The magnitude of this current is proportional to the concentration of NO.

In the above-described first example, the oxygen partial pressure in the first internal space 6 is controlled to $10^{-6}$ atm while the oxygen partial pressure in the second internal space 8, more precisely, at the three phase boundary of the internal pumping electrode 28 (second electrode), is controlled to $10^{-10}$ atm. At the same time, the location and power of the heater 36 are determined so that the temperature at the inner electrode 16 and the measuring electrode 22 disposed in the first internal space 6 is not higher than 650° C., and the temperature at the internal pumping electrode 28 in the second internal space 8 is not lower than 410° C., although the temperature of the automobile exhaust gases may vary over the full range of 300 to 900° C., for example.

While a desired temperature of the sensing element 2 may be achieved by controlling the power of the heater 36, depending upon the temperature of the measurement gas, e.g., exhaust gases, the temperature of the element may be easily controlled as desired by merely applying a suitable voltage to the heater 36, without controlling its power. That is, the sensing element 2 generally has a higher temperature at its distal end portion exposed to the exhaust gases. If the heater 36 is positioned close to the distal end of the element 2, and the second internal space 8 including the internal pumping electrode 28 is provided in the distal end portion while the first internal space 6 including the inner electrode 16 and measuring electrode 22 is located apart from the distal end, the above-indicated desired temperatures of these electrodes can be achieved by applying a suitable voltage to the heater 36.

Figure 4:
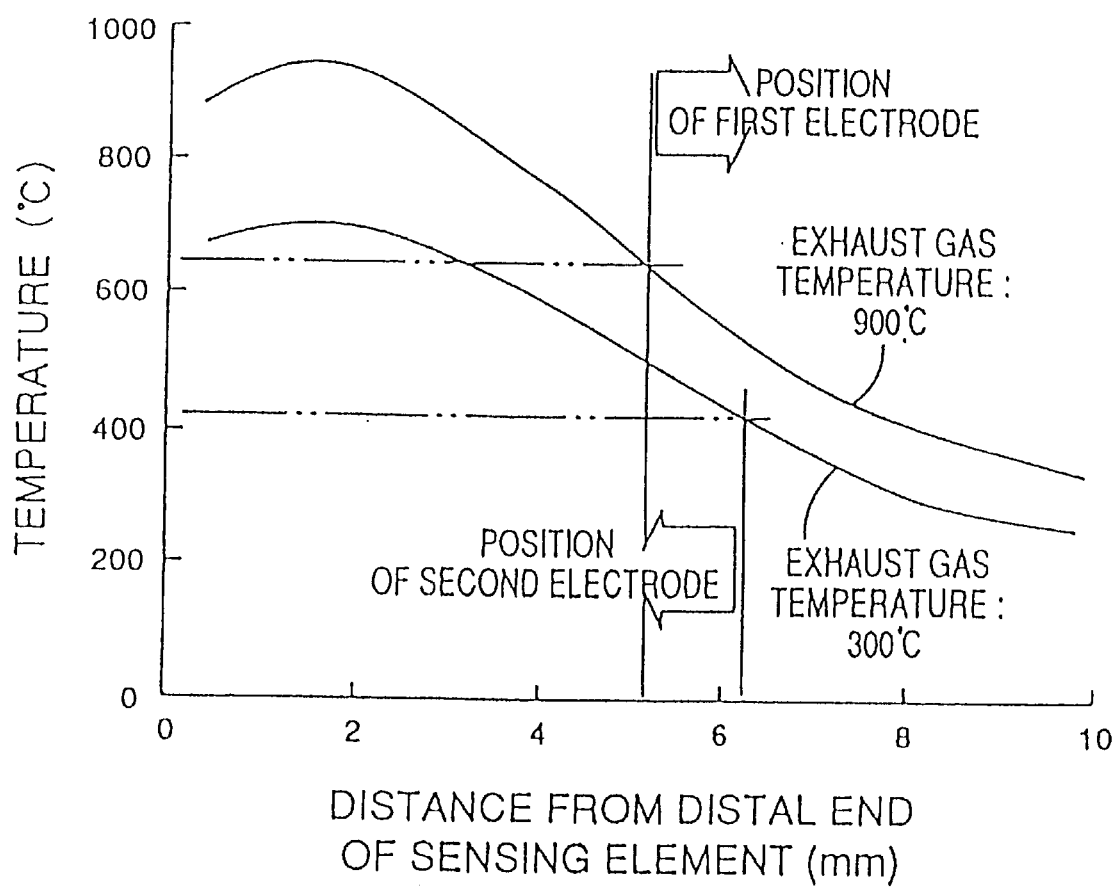
FIG. 4 is a graph showing the relationship between the temperature of the sensing element exposed to different exhaust gas temperatures, and the distance from the distal end of the element.

FIG. 4 is a graph showing results of a test for determining the location of the heater in the sensing element. A sensing element used for the test has a platinum heater embedded in a $ZrO_2$ solid electrolyte substrate, at one of various points of the element which range from 1 mm to 6 mm as measured from its distal end. The $ZrO_2$ substrate has a width of 4.2 mm, a thickness of 1.3 mm and a length of 62 mm, and the platinum heater has a heating portion having a width of 3.6 mm and a length of 5 mm, and has a resistance of 8Ω at room temperature. With this sensing element installed in an exhaust pipe of an automobile, a voltage of 12V is applied to the platinum heater, and the temperatures at the above-described various points of the element are measured when exposed to exhaust gases having 300° C. and 900° C.

As is apparent from FIG. 4, the temperature of the sensing element is 650° C. or lower in its region which is 5.2 mm or more away from the distal end of the element, when the exhaust gas has the maximum temperature of 900° C. Therefore, the first electrodes, i.e., the inner electrode 16 and measuring electrode 22 are located in the above region that is 5.2 mm or more away from the distal end. When the exhaust gas has the lowest temperature of 300° C., the temperature of the sensing element is 410° C. or higher in its region which is 0–6.2 mm away from the distal end of the element. Therefore, the second electrode, i,e, the internal pumping electrode 28, is located in the above region that is in the 0–6.2 mm distance from the distal end. In this manner, there is obtained the NOx sensor according to the present invention, in which the temperatures of the respective electrodes are controlled as shown in the graph of FIGS. 3 and 4. It is to be noted that the distribution of the temperatures in the sensing element as described above can be achieved as desired, by suitably selecting the power (resistance), size (length) and location of the heater.

Figure 5:
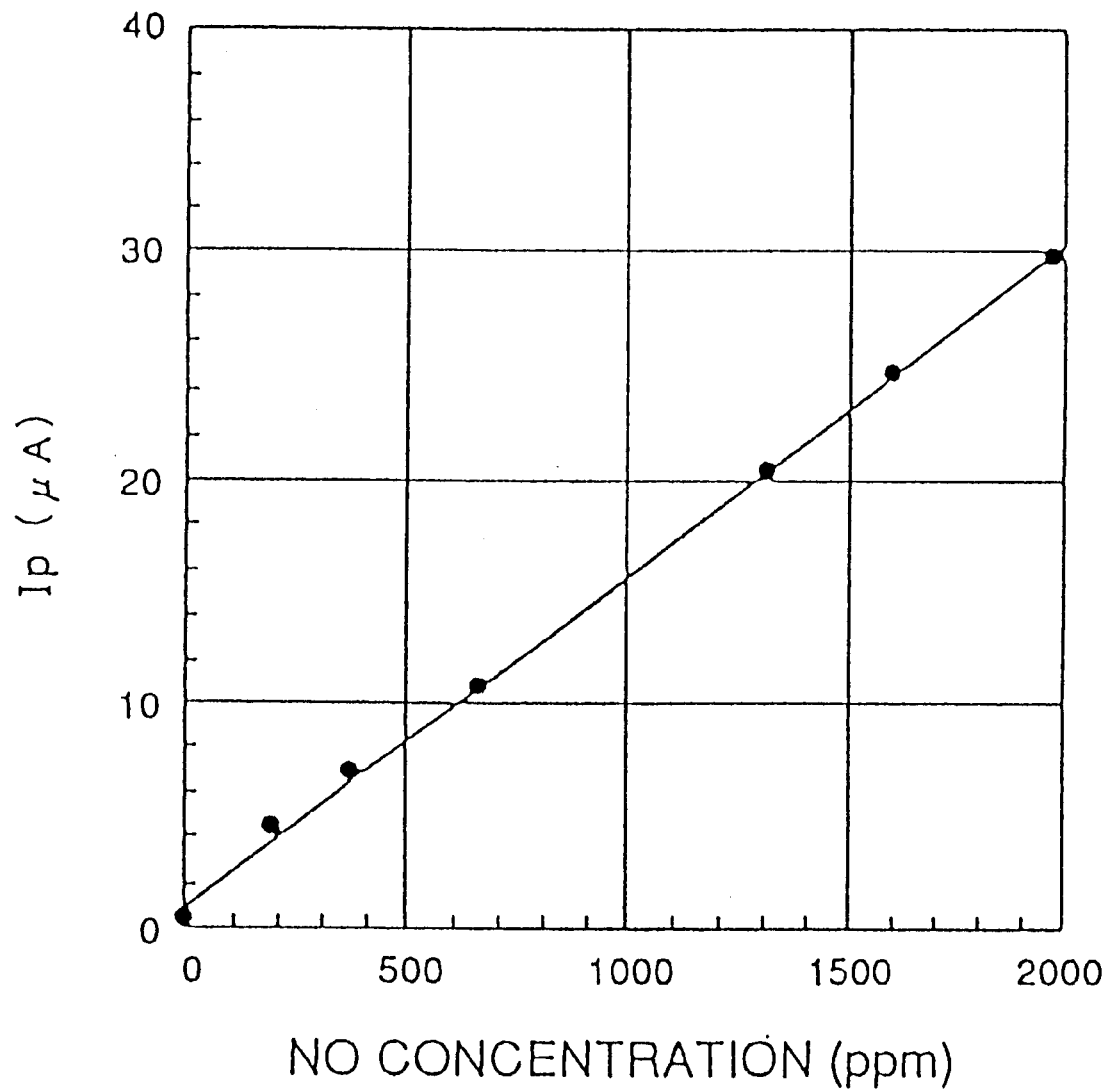
FIG. 5 is a graph showing the relationship between the NO concentration and the pumping current (Ip) obtained by the method of FIG. 3.

FIG. 5 is a graph showing the relationship between the NO concentration measured by the above-described NOx sensor, and the pumping current (diffusion limiting current: Ip). It is found in this graph that the pumping current (Ip) is linearly proportional to the NO concentration. Thus, the NO concentration can be easily obtained by measuring the current (Ip). In this case, Ip is 0.03 $\mu$A when NO is equal to 0 ppm, which means that a pumping current of 0.03 $\mu$A is required to pump out an amount of oxygen which corresponds to a difference between the oxygen partial pressure ($10^{-6}$ atm) in the atmosphere in the first internal space 6, and the oxygen partial pressure in the atmosphere in the second internal space 8, more precisely, at the three phase boundary of the internal pumping electrode 28. Although this pumping current of 0.03 $\mu$A does not affect the measurement of the NO concentration of several dozens of ppm, taking account of the sensitivity: 30 $\mu$A/2000 ppm=0.015 $\mu$A/ppm, the same pumping current may cause an error when the NO concentration to be measured is lower than 10 ppm. It is therefore preferable that the pumping current is as close to 0 as possible when NO is equal to 0 ppm. This can be achieved either by controlling the oxygen partial pressure in the atmosphere in the first internal space 6 to the possibly lowest level while avoiding reduction of NOx, or by equalizing the oxygen partial pressure in the first internal space 6 with that in the second internal space 6, measured at the three phase boundary of the internal pumping electrode 28.

Figure 6:
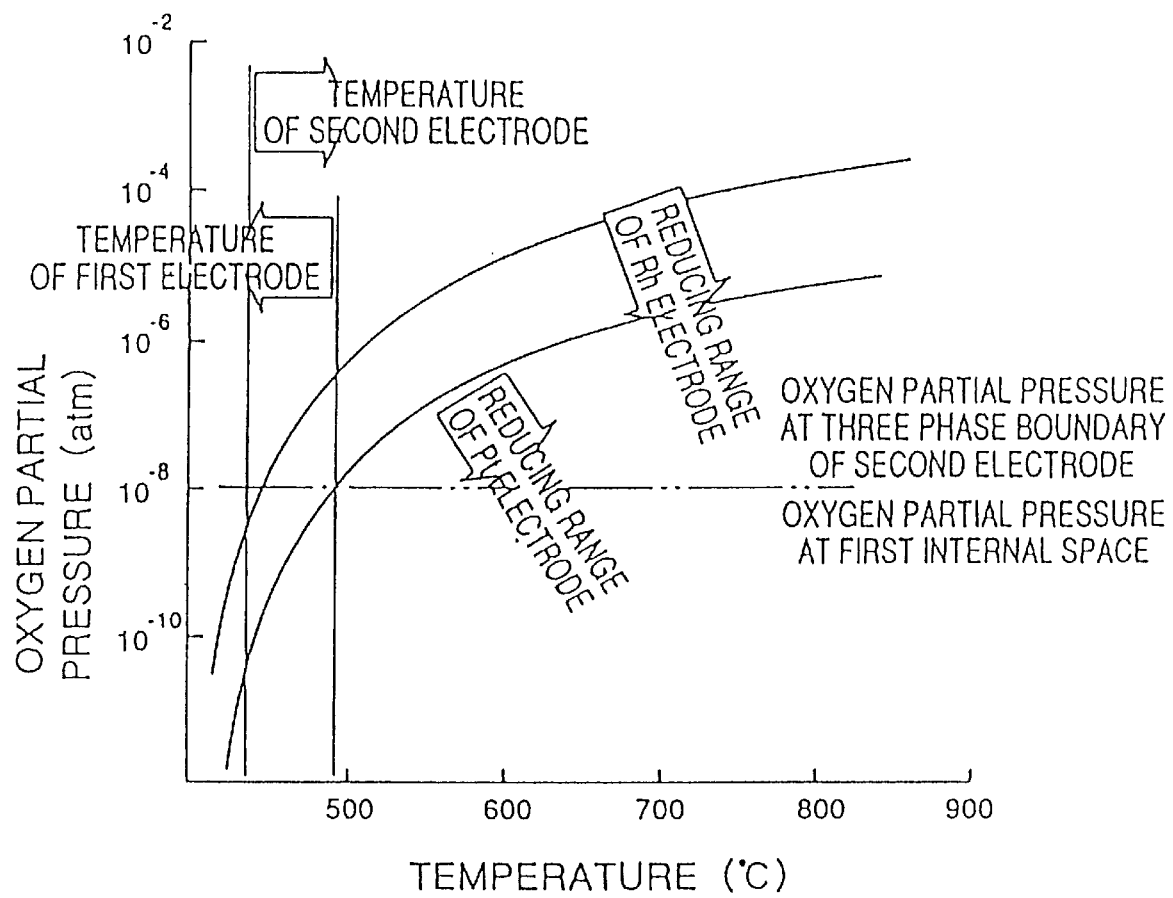
FIG. 6 is a graph showing a second method of controlling the electrode temperatures and the oxygen partial pressures in the first and second internal spaces.

FIG. 6 is a graph showing a second example of the relationship between the temperatures at the electrodes in the first and second internal spaces 6, 8, and the oxygen partial pressures in these internal spaces 6, 8 which are controlled in the manner as described above. In this example, the oxygen partial pressure in the first internal space 6, and the oxygen partial pressure at the three phase boundary of the internal pumping electrode 28 (second electrode) in the second internal space 8 are both controlled to $10^{-8}$ atm. The heater 36 is provided so that the temperature at the first electrodes (inner electrode 16 and measuring electrode 22) is 490° C. or lower, and the temperature at the second electrode (internal pumping electrode 28) is 430° C. or higher.

Figure 7:
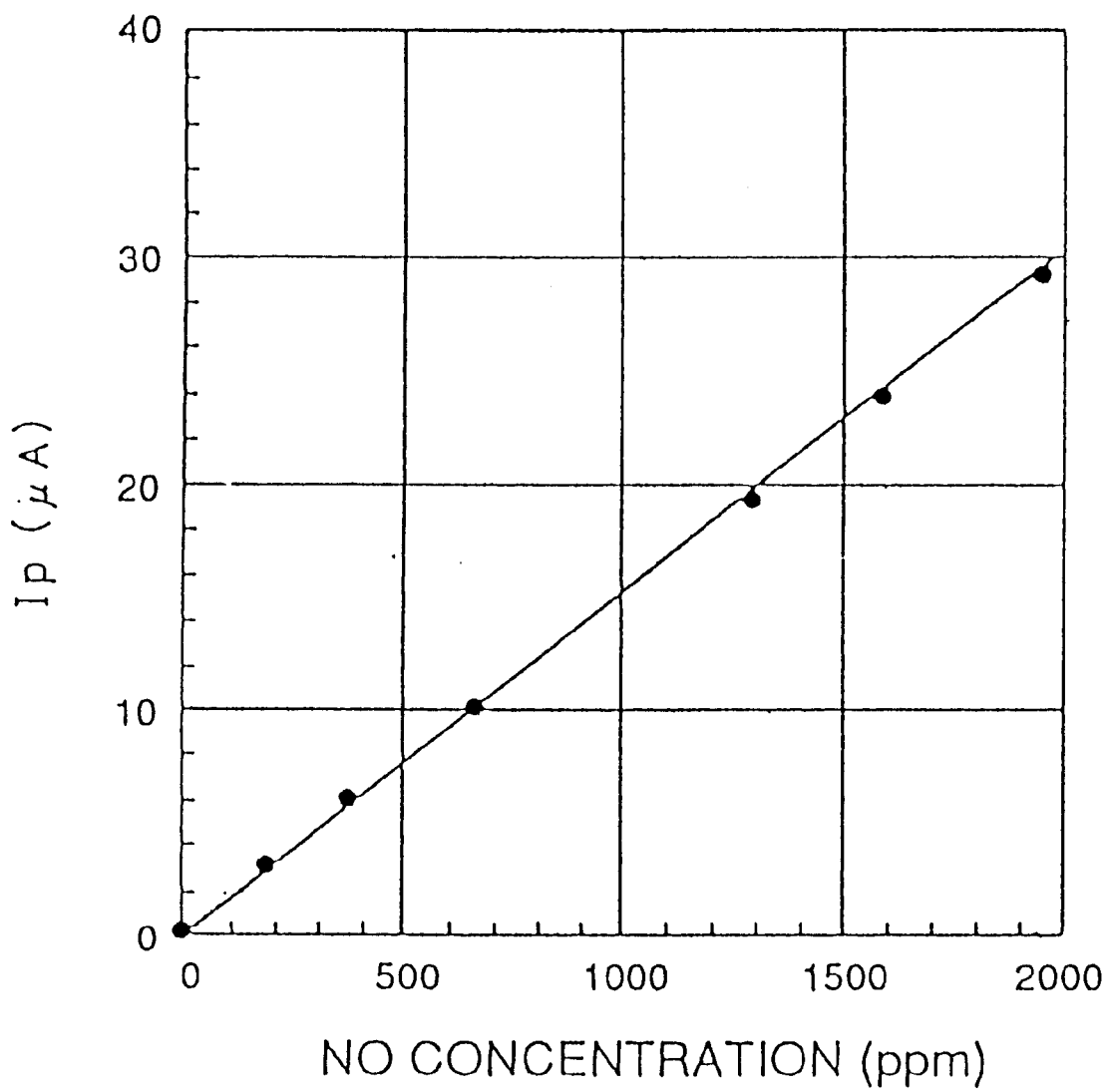
FIG. 7 is a graph showing the relationship between the NO concentration and the pumping current (Ip) obtained by the method of FIG. 6.

FIG. 7 is a graph showing the relationship between the pumping current (Ip) and the NO concentration measured by the NOx sensor of the second example. Since the oxygen partial pressures in the first internal space 6 and at the three phase boundary of the second electrode (internal pumping electrode 28) in the second internal space 8 are controlled to the same value in this example, Ip is 0 $\mu$A where NO is equal to 0 $\mu$ppm.

Figure 8:
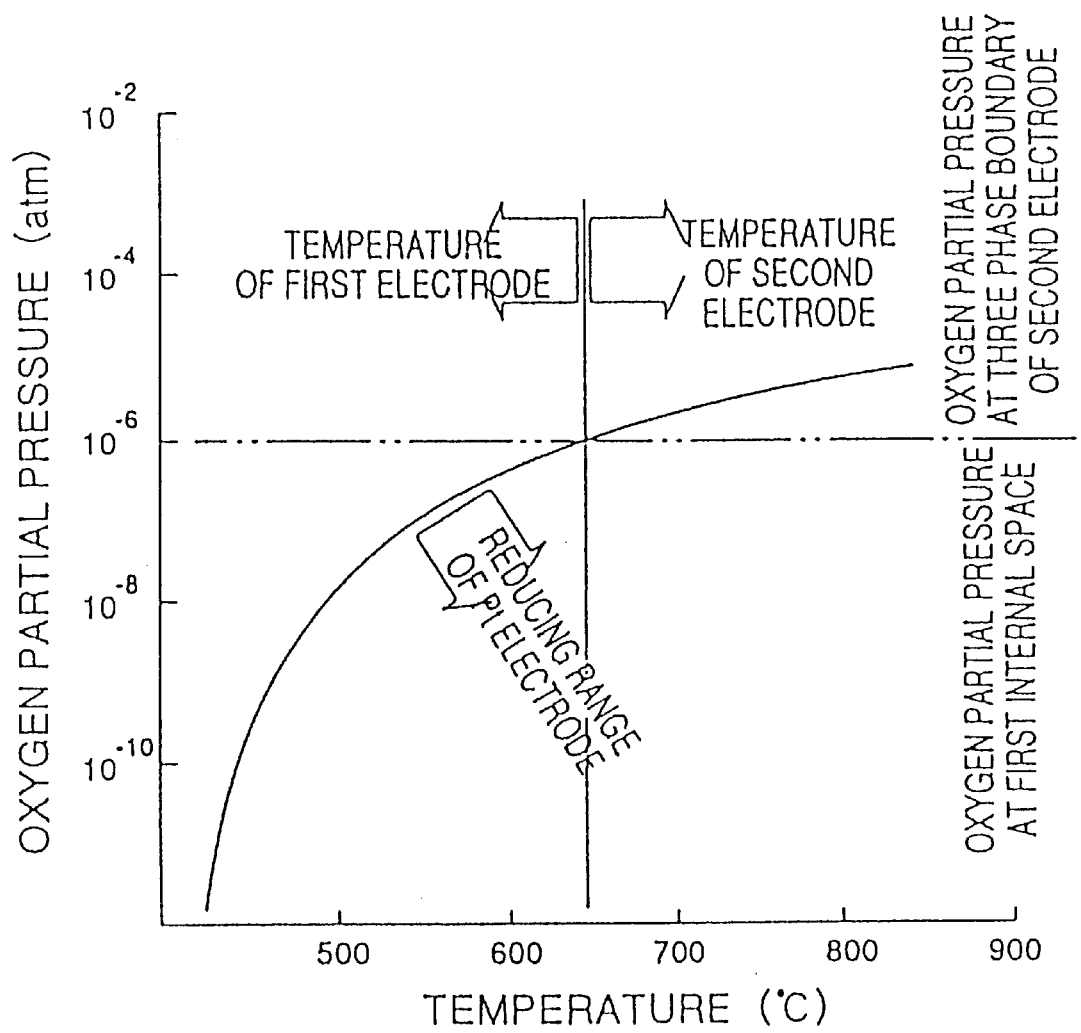
FIG. 8 is a graph showing a third method of controlling the electrode temperatures and the oxygen partial pressures in the first and second internal spaces.

FIG. 8 is a graph showing a third example of the relationship between the temperatures at the electrodes and the oxygen partial pressures. In this example, the first electrodes (inner electrode 16 and measuring electrode 22) and the second electrode (internal pumping electrode 28) are both comprised of Pt electrodes, and the oxygen partial pressures in the first internal space 6 and at the three phase boundary of the second electrode (internal pumping electrode 28) in the second internal space 8 are both controlled to $10^{-6}$ atm. The heater 36 is provided so that the temperature at the first electrodes is lower than 650° C., and the temperature at the second electrode is 650° C. or higher.

Figure 9:
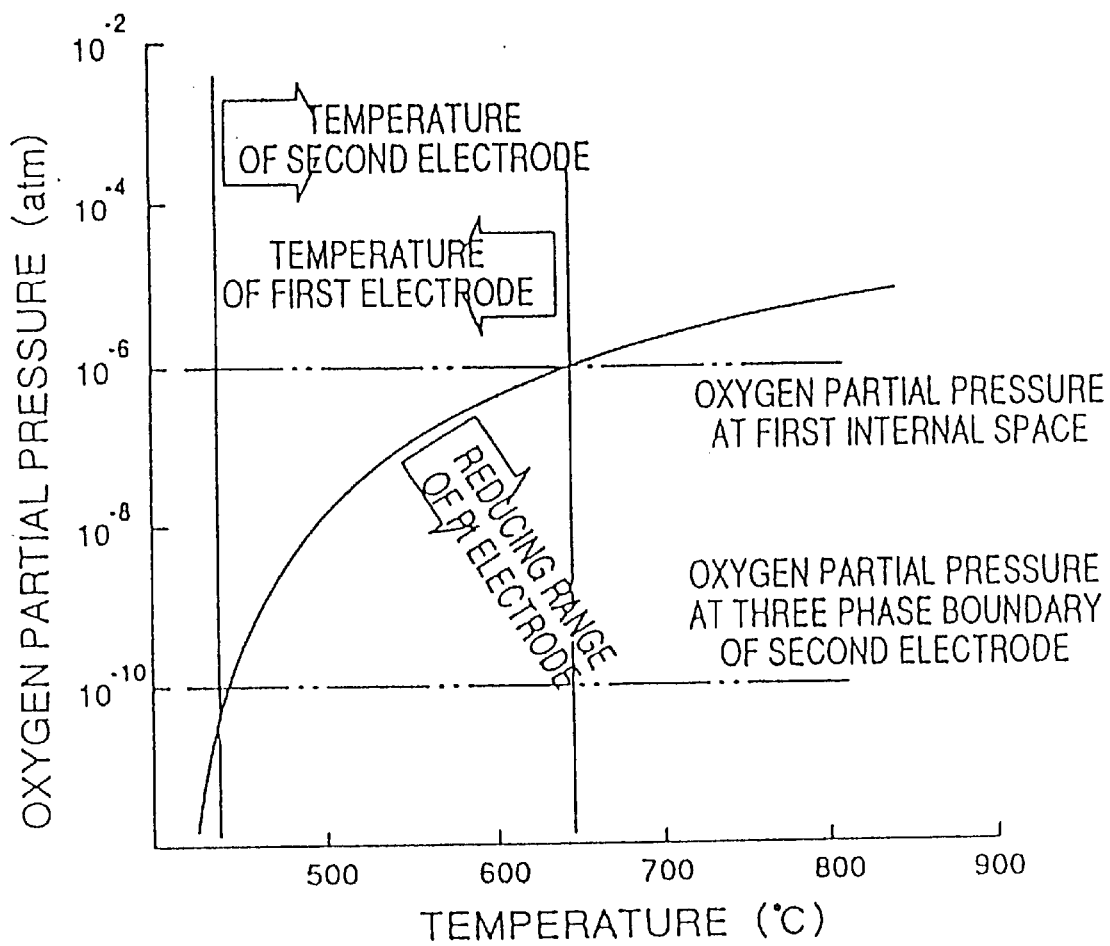
FIG. 9 is a graph showing a fourth method of controlling the electrode temperatures and the oxygen partial pressures in the first and second internal spaces.

FIG. 9 is a graph showing a fourth example of the relationship between the temperatures at the electrodes and the oxygen partial pressures. In this example, the first electrodes (inner electrode 16 and measuring electrode 22) and the second electrode (internal pumping electrode 28) are both comprised of Pt electrodes, and the oxygen partial pressure in the first internal space 6 is controlled to $10^{-6}$ atm while the oxygen partial pressure at the three phase boundary of the second electrode (internal pumping electrode 28) in the second internal space 8 is controlled to $10^{-10}$ atm. The heater 36 is provided so that the first electrodes are heated to 650° C. or lower, and the second electrode is heated up to 430° C. or higher.

Figure 10:
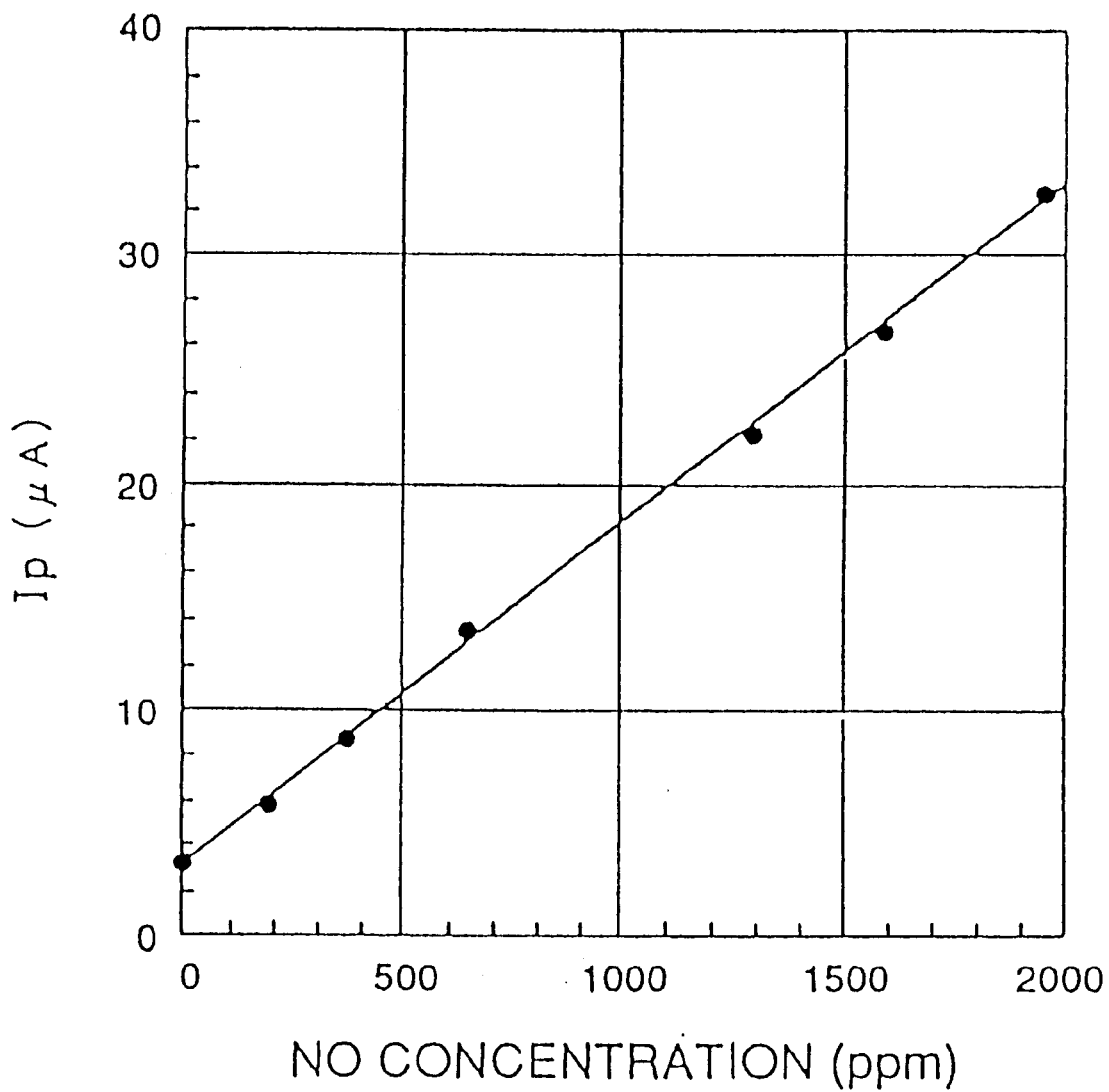
FIG. 10 is a graph showing the relationship between the NO concentration and the pumping current (Ip) obtained by the method of FIG. 9.

In the fourth example, a pumping current $IP_0$ flows when NO is equal to 0 ppm, as described above. This pumping current $IP_0$ is kept constant if the oxygen partial pressures in the first and second internal spaces 6, 8 are kept constant, and can therefore be easily subtracted from the pumping current Ip. FIG. 10 is a graph showing the relationship between the pumping current Ip and the NO concentration measured by the NOx sensor of this example.

In the above-described examples, the measurement gas is introduced into the first internal space, where the oxygen concentration of the gas is controlled to a predetermined value by the oxygen pumping action of the first electrochemical pumping cell, while the oxygen partial pressure and the temperature are suitably controlled to avoid reduction of NOx. Then, the measurement gas having the predetermined oxygen concentration is introduced from the first internal space into the second internal space, where the temperature and oxygen concentration are determined so that the NOx component in the gas is reduced at the three phase boundary of the NOx reduction catalyst (internal pumping electrode 28) disposed in the second internal space. A pumping current measured upon the oxygen pumping action of the second electrochemical pumping cell is proportional to the NOx concentration of the measurement gas. Thus, NOx can be effectively determined on the basis of the pumping current, without being affected by the oxygen concentration of the measurement gas.

In the above-described NOx sensor as the sensing device of the present invention, the first internal space 6 is positioned downstream of the first diffusion controlling passage 12, and the second diffusion controlling passage 14 is positioned downstream of the first internal space 6, as seen in the direction of flow of the measurement gas. Therefore, clogging due to oil ash may take place at the first diffusion controlling passage 12, but not likely at the second diffusion controlling passage 14. If the diffusion resistance values D1, D2 of the first and second diffusion controlling passages 12, 14 are determined to satisfy the relationship: D1+$\alpha$ ≪ D2, where $\alpha$ is a variation of the diffusion resistance due to clogging, the measurement of the NOx concentration is not affected by such clogging. Thus, the clogging of the first diffusion controlling passage 12 only results in reduction of the pumping current for keeping the oxygen concentration in the first internal space at a constant level, and will not affect the measurement of NOx since the gas containing NOx is substantially diffused through the second diffusion controlling passage 14.

In the first and second examples, the first electrodes (16, 22) disposed in the first internal space 6 are cermet electrodes containing Pt, while the second electrode (28) is a cermet electrode containing Rh. In the third and fourth examples, the first and second electrodes are both comprised of cermet electrodes containing Pt. However, the electrode materials are not necessarily limited to those as employed in the above examples. For example, the first electrode may be a cermet electrode containing Au or an alloy of Au and Pt, and the second electrode may be a Rh-containing cermet electrode. Since the Au/Pt cermet electrode as the first electrode is less likely to reduce NOx, the oxygen partial pressure and temperature in the first internal space can be more freely determined within increased allowable ranges. While metals used for the electrodes may be suitably selected from known metals, both the first and second electrodes may be Au-containing electrodes, with a Rh- or Pt-containing electrode or a catalyst superposed on the second electrode. The catalyst may be a ceramic porous layer formed of alumina, which carries thereon an NOx reducing metal. Alternatively, the first and second electrodes may be Pt-containing electrodes, with a Rh-containing catalyst electrode disposed on the second Pt electrode. It is also possible that the first and second electrodes made of the same material are exposed to different temperatures, for example.

Figure 11:
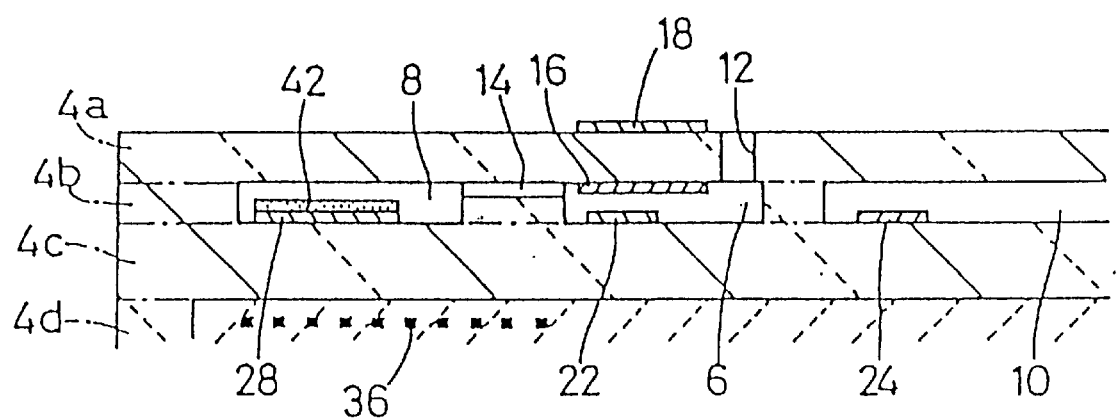
FIG. 11 is an elevational view corresponding to that of FIG. 2, showing another embodiment in which an NOx reduction catalyst is superposed on an internal pumping electrode.
Figure 12:
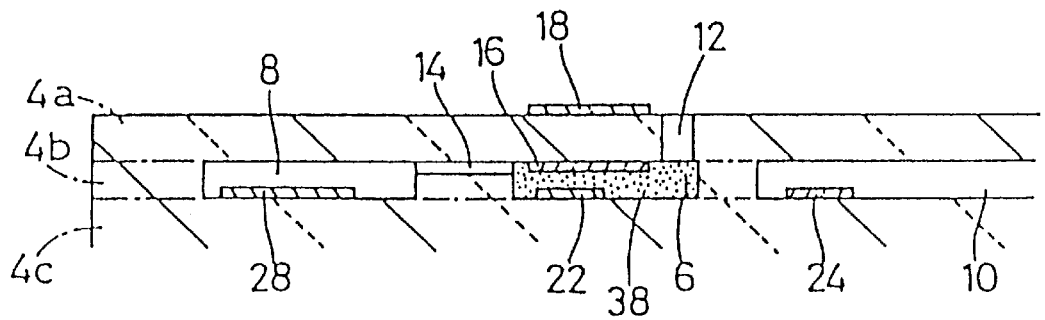
FIG. 12 is an elevational view corresponding to that of FIG. 2, showing a further embodiment in which an oxidation catalyst is provided in a first internal space.

It is desirable that the first and second electrodes are cermet electrodes comprised of a metal and a suitable ceramic material. For the second electrode which function as an NOx reduction catalyst, as in the illustrated embodiment, a porous cermet electrode is desirably employed which is formed of a ceramic and a known metal, such as Rh and Pt, capable of reducing NOx. An NOx reduction catalyst may be provided in the vicinity of the internal pumping electrode 28 disposed in the second internal space 8, or an NOx reduction catalyst 42 as shown in FIG. 11 may be laminated by printing or other method on the internal pumping electrode 28. This catalyst 42 is a porous alumina layer carrying an NOx reducing catalyst, such as rhodium. In the sensing element as shown in FIG. 11, the heater 36 is located on the side of the second internal space 8, so that the second internal space 8 is heated to a higher temperature than the first internal space 6, whereby the NOx reduction catalyst 42 performs its function more effectively.

Where the measurement gas consists of exhaust gases generated under a rich burn engine operation, the gas contains large amounts of unburned components, such as CO and HC, which may react with NOx to cause a measuring error of the NOx sensor. To avoid this, the first internal space 6 is preferably filled with an oxidation catalyst 38 formed from porous alumina, for example, for oxidizing the unburned components, such as CO and HC, in the measurement gas, as shown in FIG. 12. In this case, the polarity of the first electrochemical pumping cell is reversed with respect to that in the case of a lean burn engine operation. That is, oxygen in the measurement gas is pumped from the exterior space into the first internal space 6. The provision of the oxidation catalyst 38 in the first internal space 6 is effective for eliminating influences due to the reducing gases, such as CO and HC, even when the measurement gas is produced as a result of the rich burn operation.

While the first internal space 6 is filled with the oxidation catalyst 38 in the embodiment of FIG. 12, the catalyst 38 may be provided on a portion of the solid electrolyte layer 4c between the first diffusion controlling passage 12 and the measuring electrode 22, or may be provided by printing on the inner electrode 16. That is, the oxidation catalyst 38 may be located anywhere provided the unburned components, such as CO and HC, are oxidized before the measurement gas reaches the second internal space 8.

To oxidize the unburned components, such as CO and HC, there is no need to provide the oxidation catalyst 38. That is, the oxidation can be promoted if the inner electrode 16 functions as an oxidation catalyst. Even if the inner electrode 16 consists of an Au or Au/Pt alloy electrode which does not serve as an oxidation catalyst, the unburned components in the measurement gas can be oxidized under appropriate conditions, including the oxygen partial pressure and the temperature, in the first internal space 6. These conditions must be also advantageous for measurement of NOx, assuring the oxygen partial pressure which is as low as possible and closest to that of the second internal space 8. For example, the oxidation can readily take place in the first internal space 6 if the oxygen partial pressure is at least $10^{-10}$ atm at 500° C., and at least $10^{-15}$ atm at 600° C.

In the above-described method of measuring NOx, the measurement gas is controlled in the first internal space 6, to provide an atmosphere which is effective for measurement of NOx. More specifically, oxygen is pumped out from or pumped into the atmosphere in the first internal space 6, by the pumping action of the first electrochemical cell, so that the oxygen partial pressure in the space 6 is kept at a constant level which is almost the same as that in the second internal space 8, and which enables oxidation of the unburned components, such as CO and HC, contained in the measurement gas. Consequently, the oxidation of the unburned components is effected, thereby to avoid reaction between such unburned components and NOx, assuring more accurate measurement of the NOx concentration. This is particularly effective with respect to a measurement gas which is produced as a result of combustion under a rich burn engine operation, and thus contains considerably large amounts of carbon monoxide, hydrocarbon and other unburned components.

The oxidation of the unburned components in the measurement gas as described above is effective for eliminating any influence by the unburned components on the NOx measurement accuracy, with respect to exhaust gases produced not only under the rich burn engine operation, but also under the lean burn engine condition which may produce slight amounts of such unburned components as described above.

Figure 13:
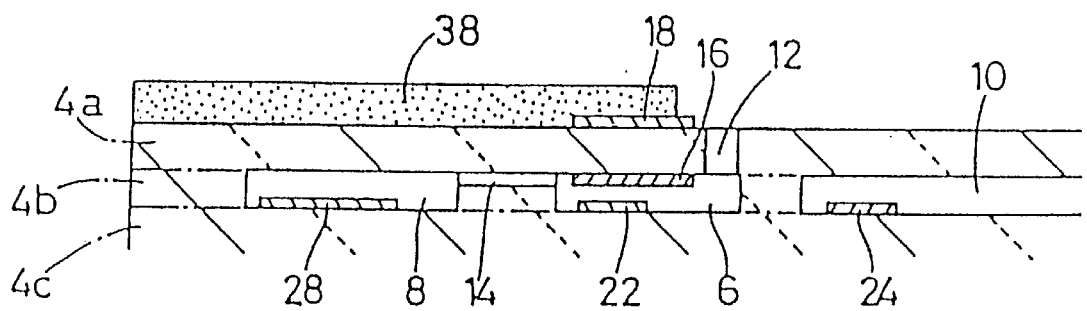
FIG. 13 is an elevational view corresponding to that of FIG. 2, showing another example of providing the oxidation catalyst.
Figure 14:
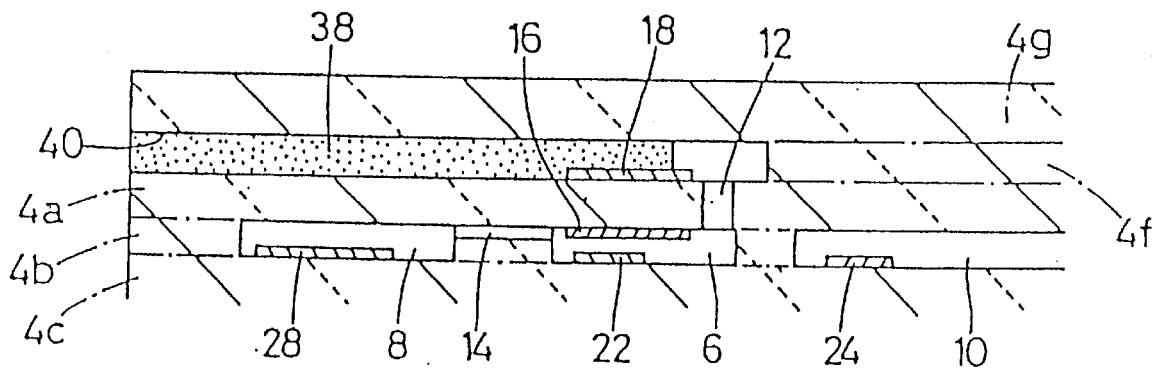
FIG. 14 is an elevational view corresponding to that of FIG. 2, showing a further example of providing the oxidation catalyst.

The oxidation catalyst 38 may be laminated on the upper solid electrolyte layer 4a, as shown in FIG. 13, such that the catalyst 38 is located in the external measurement gas space while closing an open end of the first diffusion controlling passage 12. This is effective mainly for eliminating measuring errors due to CO and HC produced when the engine operates under lean A/F condition. This embodiment is not suitable for the rich burn engine operation since the whole amounts of CO and HC cannot be oxidized due to shortage of oxygen in the measurement gas. In a further embodiment as shown in FIG. 14, additional solid electrolyte layers 4f and 4g are superposed on the solid electrolyte layer 4a, with a gas inlet channel 40 defined by these three solid electrolyte layers 4f, 4g, 4a. The oxidation catalyst 38 is located in the gas inlet channel 40. In this case, the oxidation of CO, HC and others is more effectively promoted since the oxidation catalyst 38 is located in a relatively high-temperature distal end portion of the sensor, as compared with the embodiment of FIG. 12.

To regulate the oxygen concentration at the three phase boundary of the second electrode (28) serving as an NOx reduction catalyst, in the second internal space 8, the oxygen is pumped from the second electrode (28) to the reference electrode 24 in the illustrated embodiments. However, the second electrode (28) may cooperate with the outer electrode 18 of the first electrochemical pumping cell, to constitute a second electrochemical pumping cell, so as to pump the oxygen in the second internal space 8 toward the outer electrode 18. It is also possible to provide another electrode in the second internal space 8 to pump out oxygen in the second internal space 8, in addition to the second electrode (28) as the NOx reduction catalyst. In this case, on the basis of an electromotive force induced between the NOx reduction catalyst electrode (28) and the reference electrode 24, oxygen may be pumped from the additional pump-out electrode toward the reference electrode, the outer electrode 18, or a further electrode adapted to pump out the oxygen, so as to regulate the oxygen concentration at the three phase boundary of the NOx reduction catalyst electrode.

In the illustrated embodiments, the oxygen partial pressure in the first internal space 6 is regulated by continuously varying a voltage to be applied to the pumping electrodes 16, 18 of the first electrochemical pumping cell, based on the level of the electromotive force detected at the electrochemical sensing cell. However, a constant voltage may be applied to these pumping electrodes 16, 18, or a single electrochemical cell may serve as both a pumping cell and a sensing cell at different times.

The reference electrode 24 is not necessarily held in communication with the atmosphere through the reference-gas channel 10. Rather, the reference electrode 24 may be disposed in a space in which the oxygen that is pumped out from the second electrode (28) is stored.

Figure 15:
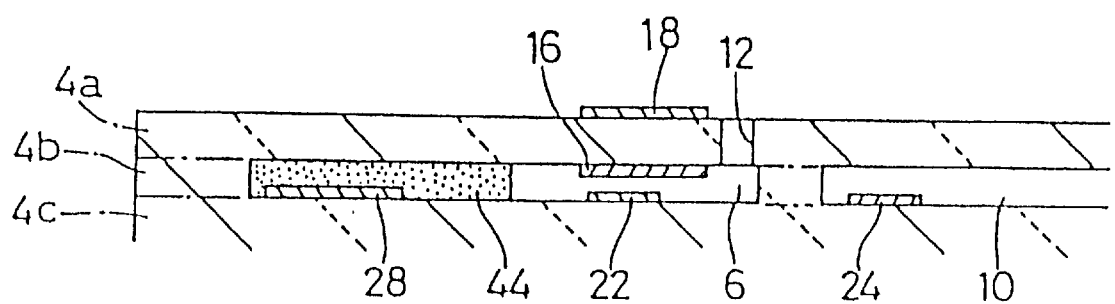
FIG. 15 is an elevational view corresponding to that of FIG. 2, showing another embodiment having different structures of second internal space and second diffusion means.

Further, the second internal space and the second diffusion means may be constituted by a space which is filled with a porous body. More specifically, the second internal space 8 and the second diffusion controlling passage 14 of the sensing element 2 shown in FIG. 2 may be replaced by an arrangement as shown in FIG. 15, in which an internal space adjacent to the first internal space 6 is filled with a porous body 44 made of alumina, for example, to provide both the second diffusion means and the second internal space. This arrangement simplifies the internal structure of the NOx sensor. In this embodiment, the diffusion resistance of the second diffusion means (44) is determined to be larger than that of the first diffusion controlling passage 12, such that the atmosphere in the first internal space 6 is not influenced by the atmosphere in the second internal space.

Figure 21:
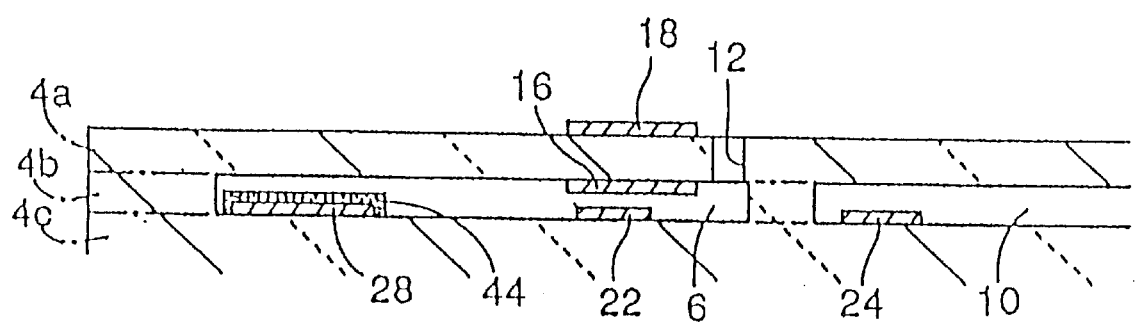
FIG. 21 is an elevational view corresponding to that of FIG. 2, showing another embodiment in which the second internal space and second diffusion means have different structures than those of FIG. 15.

The porous body 44 may be printed on the internal pumping electrode 28, as shown in FIG. 21. In this arrangement, the porous body 44 constitutes the second diffusion means, and the porous body 44 itself substantially provides the second internal space.

Figure 16:
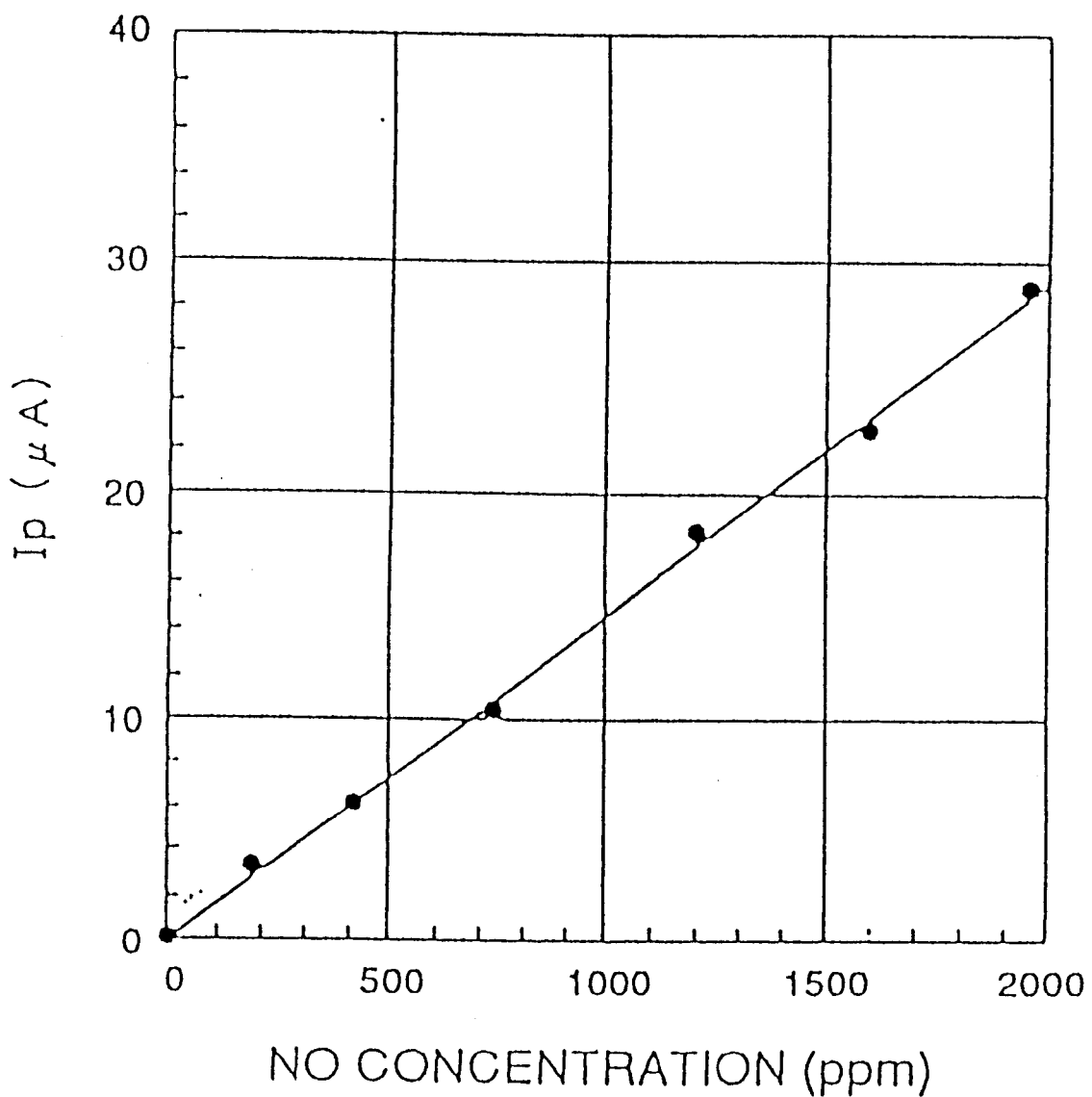
FIG. 16 is a graph showing the relationship between the NO concentration and the pumping current (Ip) obtained in the embodiment of FIG. 15.

In operation of the sensing element 2 constructed as described above, a voltage applied between the two electrodes 16, 18 of the first electrochemical pumping cell is controlled so that an electromotive force of 203 mV is induced at 500° C. between the measuring electrode 22 in the first internal space 6, and the reference electrode 24. At the same time, a constant voltage is applied between the internal pumping electrode 28 and the reference electrode 24 of the second electrochemical pumping cell, so that an electromotive force of 449 mV is induced at 700° C. between these electrodes 28, 24. In this condition, the NO concentration linearly varies with the pumping current (Ip) of the second electrochemical pumping cell, as shown in the graph of FIG. 16. Accordingly, the NO concentration is determined by measuring the magnitude of the pumping current (Ip).

The arrangement of the sensing element as shown in FIG. 15 may be modified such that the porous structure of the second diffusion means 44 carries therein an NOx reduction catalyst, or such that an oxidation catalyst for oxidizing the unburned components, such as CO and HC, is disposed in the first internal space 6. Thus, the present sensing element may be modified as needed, while assuring NOx detecting characteristics similar to those of the sensing element of FIG. 15.

The materials for the electrodes (16, 22) disposed in the first internal space 6 and the electrode (28) disposed in the second internal space (second diffusion means 44) are suitably selected such that the electrode (28) in the second internal space has the same or higher capability of reducing NOx than the electrodes (16, 22) in the first internal space 6. In addition, an NOx reduction catalyst layer may be provided on the electrode (28) in the second internal space.

The location of the reference electrode and the the reference-gas chamber and the kind of the reference gas are suitably selected, such that the electromotive force determined according to the Nernst equation is induced between the measuring electrode in the first internal space 6 and the reference electrode.

The position and power of the heater are suitably selected such that the temperature at the electrodes in the first internal space 6 is lower than the temperature at the electrode in the second internal space (second diffusion means 44).

The NOx sensor according to the present invention may have the first and second diffusion means in the form of a narrow, flat space having a predetermined diffusion resistance. The flat space is formed in the sensing element so as to be open to the external measurement-gas space, as shown in FIG. 17 by way of example.

Figure 17:
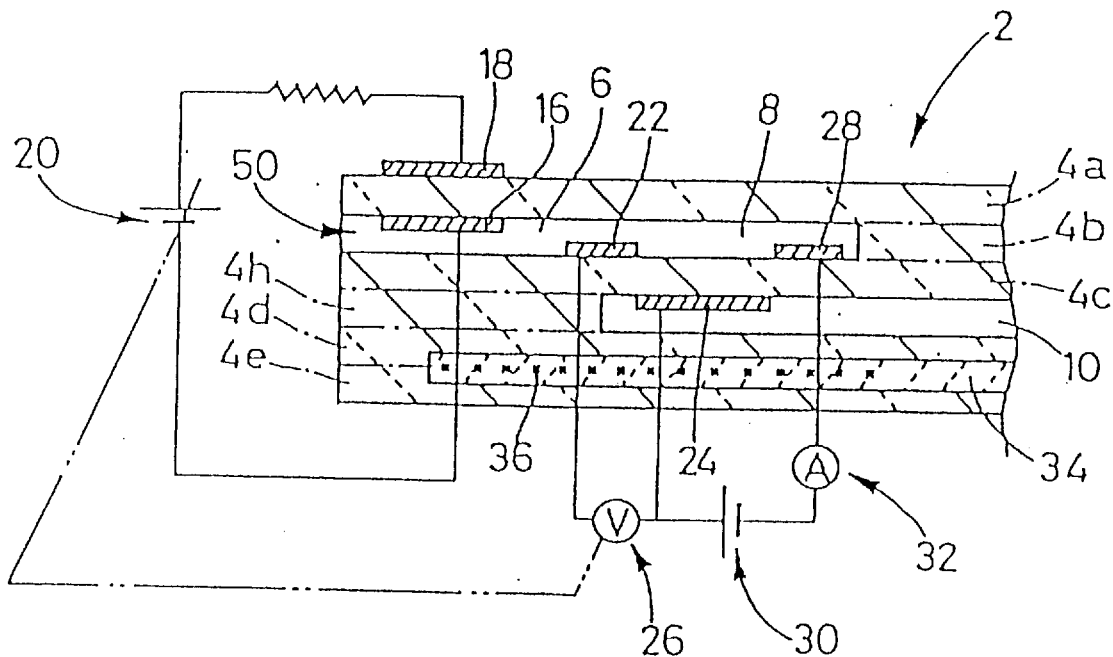
FIG. 17 is an elevational view corresponding to that of FIG. 2, showing a sensing element as part of another embodiment of the NOx sensor of the present invention.

The sensing element 2 as shown in FIG. 17 has an integral laminar structure including six oxygen-ion conductive solid electrolyte layers 4a, 4b, 4c, 4h, 4d, 4e which are superposed on each other in this order. The second uppermost solid electrolyte layer 4b has a rectangular cutout or notch at its distal end portion, which provides a narrow, flat space 50 having a predetermined diffusion resistance. The flat space 50 is open at the distal end of the sensing element 2, and extends over a suitable length in the longitudinal direction of the element 2. That is, the flat space 50 has an elongate, rectangular shape as seen in a plane parallel to the major surfaces of the sensing element 2, and is open at one of the opposite short sides to the external measurement-gas space.

In operation, the external measurement gas is introduced through the opening of the flat space 50, and reaches an innermost part of the flat space 50, under a predetermined diffusion resistance. Thus, the flat space 50 itself constitutes the first and second diffusion means. The inner electrode (pumping electrode) 16 of the first electrochemical pumping cell is provided in a portion of the flat space 50 adjacent to its opening, which portion forms the first internal space 6, while the internal pumping electrode 28 of the second electrochemical pumping cell is provided in a deeper portion of the flat space 50 inside of the first internal space 6, which portion forms the second internal space 8.

In the instant embodiment, reference-gas channel 10 is formed through the solid electrolyte layer 4h, such that the channel 10 is open at a proximal end of the sensing element, for communication with the atmosphere. Reference electrode 24 disposed in the reference-gas channel 10 cooperates with the measuring electrode 22 provided in the flat space 50 to constitute the electrochemical sensing cell, and cooperates with the internal pumping electrode 28 to constitute the second electrochemical pumping cell. Thus, the reference electrode 24 also serves as one of the pumping electrodes.

Figure 25:
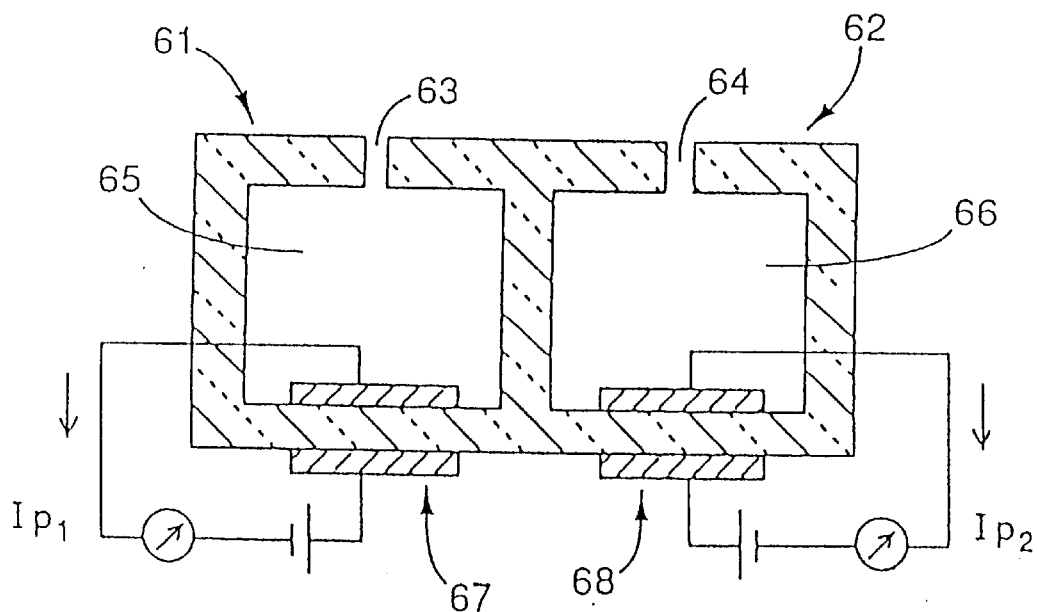
FIG. 25 is a cross sectional view of a known sensing element, for explaining a known method of measuring a gas component.

The other parts of the NOx sensor as shown in FIG. 17 are similar to those of the NOx sensor of FIG. 2, and the same reference numerals are used in the figures for the corresponding elements, of which no detailed description will be provided. The specific structures for the flat space 50 and the reference-gas channel 10 formed in the sensing element 2 are shown in detail in FIGS. 25 and 26 of U.S. Pat. No. 4,645,572 (which is incorporated herein by reference), from which the structure of the sensing element of FIG. 17 is to be understood.

Figure 18:
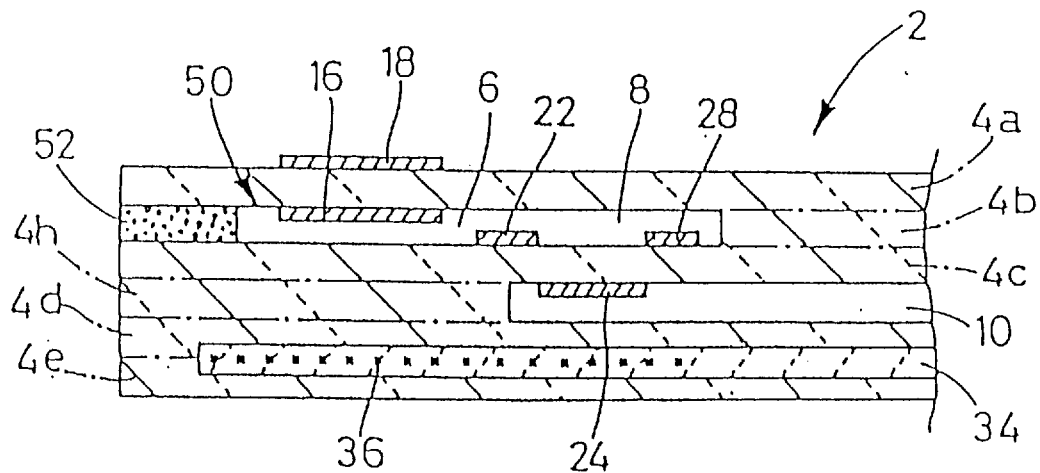
FIG. 18 is an elevational view corresponding to that of FIG. 17, showing a modified example of the sensing element of FIG. 17.

FIG. 18 shows a modified embodiment of the sensing element 2 as shown in FIG. 17. In this embodiment, an open end portion of the flat space 50 is filled with a porous body 52 having a predetermined diffusion resistance. The measurement gas is introduced through the porous body 52 into the flat space 50, under the predetermined diffusion resistance, and the introduced gas is subjected to an oxygen pumping action of the first oxygen pumping means, in the first internal space 6 provided by a portion of the flat space 50 adjacent to the porous body 52. The provision of the porous body 52 is advantageous in that the diffusion of the gas into the first internal space 6 can be controlled with high reliability, and that unburned components, such as CO and HC, are effectively oxidized at the porous body 52.

Figure 18A:
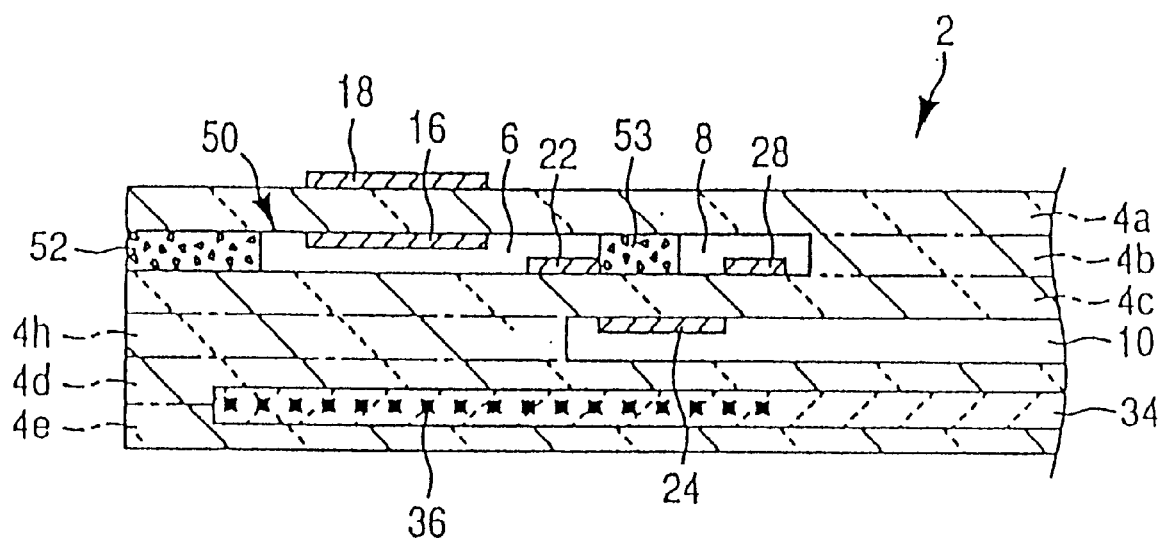
FIG. 18A is an elevational view showing another modified example of the sensing element of FIG. 17.

The sensing element 2 of FIG. 18 may be modified as shown in FIG. 18A. In this modified arrangement, an inner portion of the flat space 50 is filled with another porous body 53 having a predetermined diffusion registance. The porous body 53 is located between the electrodes 22, 28, so that the measurement gas flow from the first internal space 6 into the second internal space 8 through the porous body 53 under the predetermined diffusion resistance. In this embodiment of FIG. 18A, the porous bodies 52 and 53 function as first and second diffusion means, respectively.

In the illustrated embodiments of the NOx sensor, the effective decomposition and reduction of NOx are achieved due to a temperature difference between the first and second internal spaces 6, 8. However, the atmospheres in the first and second internal spaces 8 do not necessarily have different temperatures. In the example of FIG. 3, for instance, if the temperature of both of the first and second internal spaces 6, 8 is set to 600° C., the Pt electrode (16) disposed in the first internal space 6 will not reduce NOx under the oxygen partial pressure of about $10^{-6}$ atm or higher, while the Rh electrode (28) disposed in the second internal space 8 will reduce NOx under the oxygen partial pressure of $10^{-5}$ atm or lower. It is therefore possible to measure NOx with high accuracy even when both the first and second internal spaces 6, 8 have the same temperature of 600° C., if the oxygen partial pressure of the atmosphere in the first internal space 6 is controlled to $10^{-6}$ atm or higher, and the oxygen partial pressure of the atmosphere in the second internal space 8 is controlled to $10^{-5}$ atm or lower.

If the electrodes having little or no capability of reducing NOx, such as those containing Au or an alloy of Au and Pt, are employed, the measurement of NOx can be effected under a condition where the temperature of the first internal space is higher than that of the second internal space. For example, the alloy electrode containing Pt and 1% of Au, which does not reduce NOx at 800° C. under the oxygen partial pressure of $10^{-15}$ atm, may be employed for measurement of NOx, even if the first internal space is kept at 800° C. with the oxygen partial pressure of $10^{-10}$ atm, and the second internal space is kept at 600° C. with the oxygen partial pressure of $10^{-10}$ atm.

Figure 19:
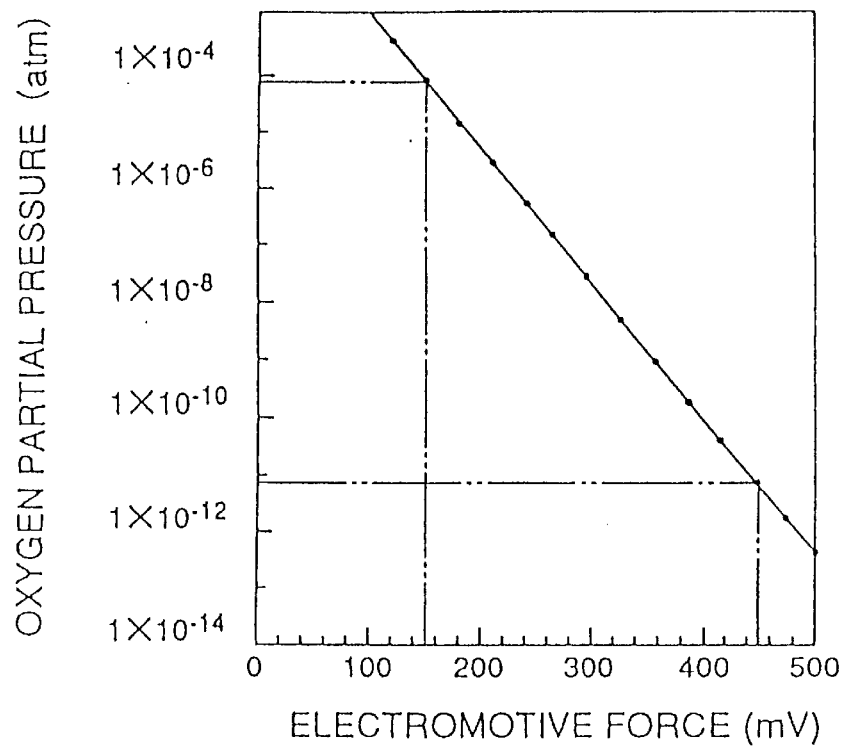
FIG. 19 is a graph showing the relationship between the electromotive force and the oxygen partial pressure at a temperature of 600° C.
Figure 20:
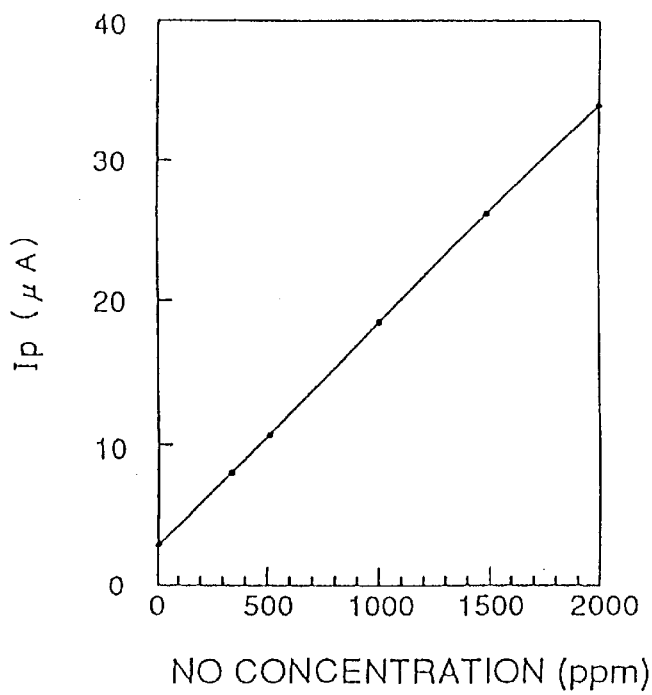
FIG. 20 is a graph showing the relationship between the NO concentration and the pumping current detected when different voltages are applied to the first and second electrochemical pumping cells while the first and second internal spaces are kept at 600° C.

FIG. 19 is a graph showing the relationship between the electromotive force and the oxygen partial pressure at a temperature of 600° C. If the oxygen partial pressure of the atmosphere in the first internal space 6 is regulated so that the electromotive force at the measuring electrode 22 of the electrochemical sensing cell is 150 mV, the oxygen partial pressure in the first internal space 6 becomes equal to about $10^{-4}$ atm, and therefore NOx is not reduced in the first internal space 6. If 450 mV is applied to the internal pumping electrode 28 of the second electrochemical pumping cell, which electrode is disposed in the second internal space 8, the oxygen partial pressure at the three phase boundary of the pumping electrode 28 becomes equal to about $10^{-11}$ atm, and therefore NOx is reduced at the internal pumping electrode 28. The oxygen generated by the reduction of NOx can be detected by the pumping current of the second electrochemical pumping cell. The graph of FIG. 20 shows the relationship between the NO concentration and the pumping current (Ip).

Figure 22:
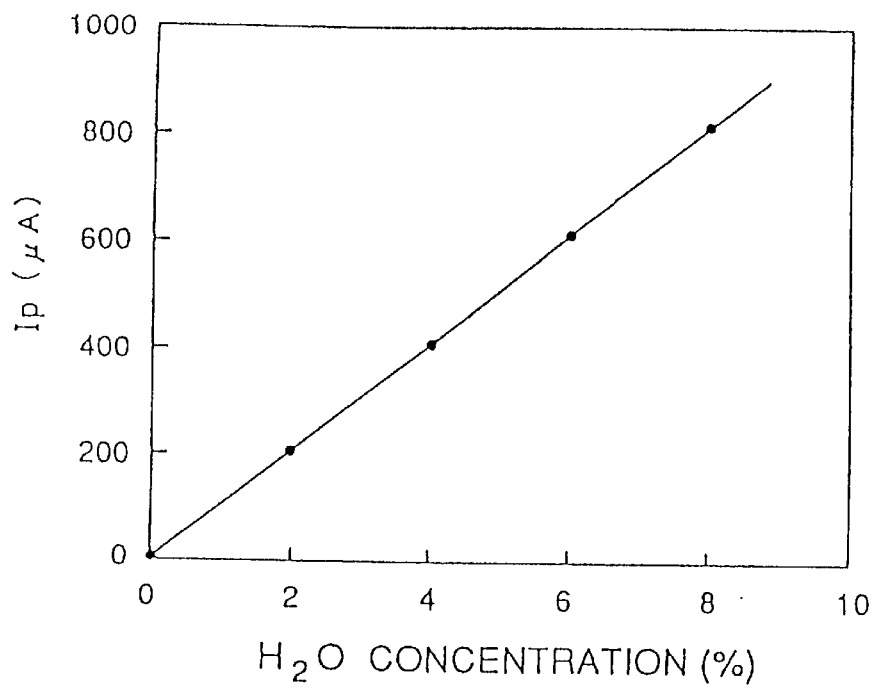
FIG. 22 is a graph showing the relationship between the $H_2O$ concentration and the pumping current (Ip) upon measurement of $H_2O$ in which the first and second internal spaces are kept at 700° C.

While the sensors of the illustrated embodiments are adapted for measuring NOx as a component of the measurement gas, it is to be understood that the present invention may be equally advantageously practiced for measurement of other gas components containing bonded oxygen, such as $H_2O$ or $CO_2$, which measurement may be affected by oxygen present in the measurement gas.

Where the sensing element 2 as shown in FIGS. 1 and 2 is used for measuring $H_2O$ (water) in the measurement gas, the atmosphere in the first internal space 6 is initially subjected to the oxygen pumping action of the first electrochemical pumping cell, so that the oxygen partial pressure is controlled to the possibly lowest level, e.g., $10^{-10}$ atm, under which $H_2O$ is not decomposed. Then, the measurement gas (the atmosphere in the first internal space 6) having the constant low level of the $O_2$ concentration is introduced into the second internal space 8, through the second diffusion controlling passage 14. With the power supply 30 applying a fixed voltage of 1.5V between the electrodes 24, 28 of the second electrochemical pumping cell, $H_2O$ contained in the atmosphere in the second internal space 8 is decomposed into $H_2$ and $O_2$, and the thus produced $O_2$ is pumped out by the pumping cell at the same time. The pumping current detected by the ammeter 32 upon the pumping action of the second electrochemical pumping cell is proportional to the $H_2O$ concentration of the atmosphere in the second internal space 8. Since oxygen in the measurement gas is reduced down to $10^{-10}$ atm (0.0001 ppm) in the first internal space 6, the above pumping current substantially represents the oxygen generated by decomposition of $H_2O$. FIG. 22 is a graph showing the relationship between the $H_2O$ concentration and the pumping current (Ip) when the first and second internal spaces 6, 8 are both heated up to 700° C.

In the measurement of $H_2O$ as described above, a pumping voltage of the second electrochemical pumping cell is controlled to not less than 1V so as to decompose $H_2O$ in the atmosphere. If the voltage is less than 1V, $H_2O$ will not be fully decomposed. At the same time, the pumping voltage is desirably controlled to not higher than 3V, since the solid electrolyte material, such as $ZrO_2$, may be decomposed with a result of reduced mechanical strength, if a voltage higher than 3V is applied to effect the pumping action for a long time. Accordingly, the pumping voltage is preferably determined in the range of 1.2V to 2.5V.

The sensing element 2 as shown in FIGS. 1 and 2 may also be used for measuring $CO_2$ contained in the measurement gas, in the same manner as described above with respect to $H_2O$. In the measurement of $CO_2$, the oxygen partial pressure of the atmosphere in the first internal space 6 is first controlled to the possibly lowest level, e.g., $10^{-10}$ atm, under which $CO_2$ is not decomposed. Then, the atmosphere having the constant low level of the $O_2$ concentration is introduced into the second internal space 8, through the second diffusion controlling passage 14. With the power supply 30 applying a fixed voltage of 1.5V to the second electrochemical pumping cell, the oxygen is pumped out from the internal pumping electrode 28 toward the reference electrode 24. During this pumping action, $CO_2$ in the second internal space 8 is decomposed into CO and $O_2$, and the thus produced $O_2$ is pumped out by the pumping cell at the same time. The pumping current thus obtained is proportional to the $CO_2$ concentration. Since oxygen in the measurement gas is reduced down to $10^{-10}$ atm (0.0001 ppm) in the first internal space 6, the above pumping current substantially represents the oxygen generated by decomposition of $CO_2$.

Figure 23:
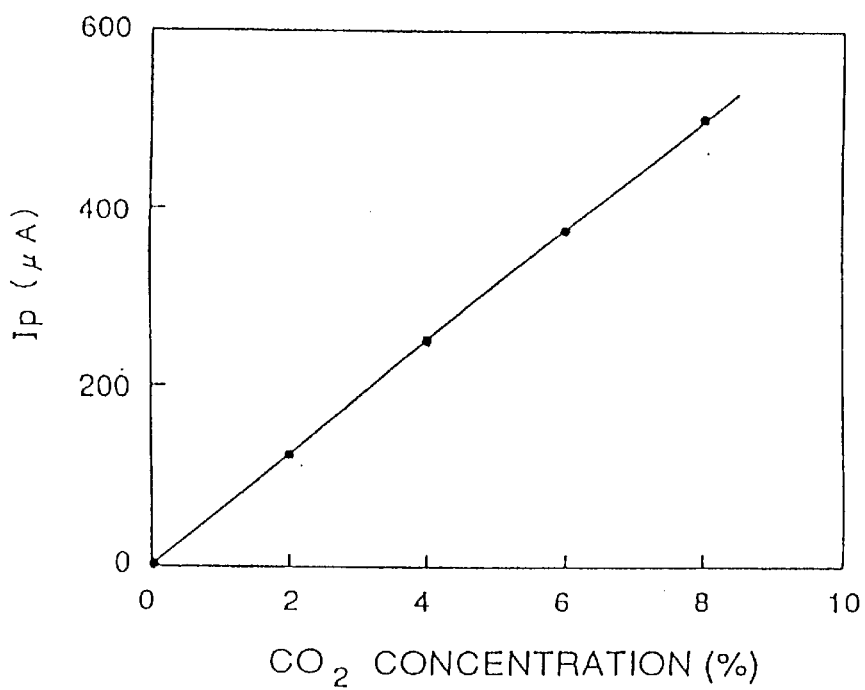
FIG. 23 is a graph showing the relationship between the $CO_2$ concentration and the pumping current (Ip) upon measurement of $CO_2$ in which the first and second internal spaces are kept at 700° C.

FIG. 23 is a graph showing the relationship between the $CO_2$ concentration and the pumping current (Ip) when the first and second internal spaces 6, 8 are both heated up to 700° C.

In the measurement of $CO_2$ as described above, a pumping voltage of the second electrochemical pumping cell is controlled to be not less than 1V so as to decompose $CO_2$ in the atmosphere. If the voltage is less than 1V, $CO_2$ will not be fully decomposed. At the same time, the pumping voltage is desirably controlled to be not higher than 3V, since the solid electrolyte material, such as $ZrO_2$, may be decomposed with a result of reduced mechanical strength, if a voltage higher than 3V is applied to effect the pumping action for a long time. Accordingly, the pumping voltage is preferably determined in the range of 1.2V to 2.5V.

Thus, the concentration of the gas component having bonded oxygen, such as $H_2O$ and $CO_2$, can be obtained by detecting the pumping current (Ip) for pumping out the oxygen generated upon decomposition of the gas component in the second internal space 8, in the same manner as the NOx concentration is determined. In this connection, a suitable decomposing catalyst may be provided in the second internal space 8, as in the case of NOx, so as to positively promote decomposition of the gas component, such as $H_2O$ and $CO_2$.

While the present invention is particularly advantageously practiced for measuring a component containing combined gas, such as NOx, $H_2O$, or $CO_2$, in a measurement gas, the present invention is not limited to these applications but is equally applicable for measurement of any gas component, provided the measurement is affected by oxygen in the measurement gas. Upon measurement of $H_2$ or $NH_3$ in a measurement gas, for example, these components may be burnt due to oxygen in the gas, resulting in deteriorated measuring accuracy. If the oxygen in the measurement gas is removed in the first internal space according to the present invention, the $H_2$ or $NH_3$ concentration can he measured with high accuracy in the second internal space.

The concentration of each of $H_2$, $NH_3$, and other various gas components present in the atmosphere in the second internal space may be measured by a selected one of known detecting means. More specifically, $H_2$ may be measured by using a proton pump constructed similarly to the oxygen pumping means. The proton pump consists of a proton-ion conductive solid electrolyte layer, and a pair of electrodes formed in contact with the layer. In operation, a current is applied to the pair of electrodes, so as to pump out $H_2$ from the second internal space, and the $H_2$ concentration is determined by detecting the pumping current. Likewise, $NH_3$ is measured by 1) decomposing $NH_3$ into $H_2$ and $N_2$ in the second internal space, 2) pumping out the $H_2$ thus generated by means of the proton pump as described above, and 3) detecting the pumping current during the pumping action, so as to determine the $NH_3$ concentration.

As described before, it is desirable that the inner pumping electrode 16 and the measuring electrode 22 in the first internal space 6 be made of a material which is less likely to cause reduction of NOx. In this respect, these electrodes 16, 22 are preferably made of a material (e.g., cermet) including an alloy which consists of a suitable amount of Au and the balance consisting principally of an element selected from the platinum group, for instance, Pt, Rh or Pd.

The content of Au in the Au—Pt or Au—Rh alloy should be within a range between 0.01 wt. % and 36 wt. %. To reduce the NOx reducing ability of the electrodes 16, 22 in the first internal space 6, the content of Au should not be smaller than 0.01 wt. %., as described below in detail by reference to FIG. 29. To prevent abnormal growth of grains of the alloy in the powder form, the Au content should not be larger than 36 wt. %. The abnormal growth of the grains results in difficult firing or baking of a green paste of the electrode material including the alloy, at a temperature not lower than 1300° C. Usually, the green paste for the electrode material is applied by printing to green ceramic sheets for the oxygen-ion conductive solid electrolyte layers, and the green electrode paste applied in desired patterns are fired into the electrodes. The firing temperature should be 1300° C. or higher, for permitting co-firing of the green electrode paste with the green ceramic sheets to produce an integral sensing element. For this reason, the Au content of the alloy should be 36 wt. % or smaller.

A test was conducted using specimen sensing elements as shown in FIG. 18A, wherein the electrodes 16 and 22 were formed of cermet materials which include zirconia and respective Au—Pt alloys whose Au contents are 1 wt. %, 10 wt. %, 20 wt. %, 35 wt. % and 40 wt. %, respectively. The impedance of the first pumping cell which includes the electrodes 16, 18 was measured, and the pumping current of the second pumping cell which represents the NOx concentration of the measurement gas was measured at the NO concentration values of 300 ppm and 500 ppm. The measured impedance and pumping current values of the specimens are shown in FIGS. 26 and 27, respectively.

Figure 26:
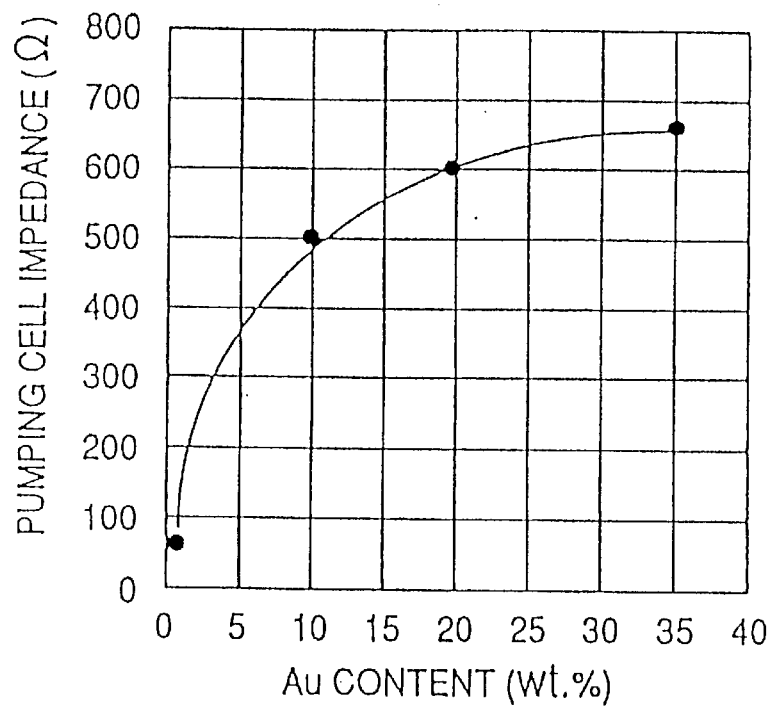
FIGS. 26 and 27 are graphs indicating influences of the Au content of a Au—Pt alloy used for the electrodes in the first internal space, on the impedance of the pumping cells and the sensitivity of the pumping current of the second pumping cell to a change in the NO concentration.

It will be understood from FIG. 26 that the impedance of the pumping cells increases as the Au content of the Au—Pt alloy increases. The impedance of the pumping cells wherein the Au-content of the electrodes 16, 22 is 35 wt. % is about nine times as high as that of the pumping cells wherein the Au-content is 1 wt. %. In this respect, it is noted that an increase in the Au content causes a decrease in the melting point of the Au—Pt alloy, which in turn causes a decrease in the porosity of the electrodes, resulting in a decrease in the three-phase boundary surface area of the electrodes and an increase in the gas diffusion resistance of the electrodes. Thus, the impedance increases with an increase in the Au content.

Figure 27:
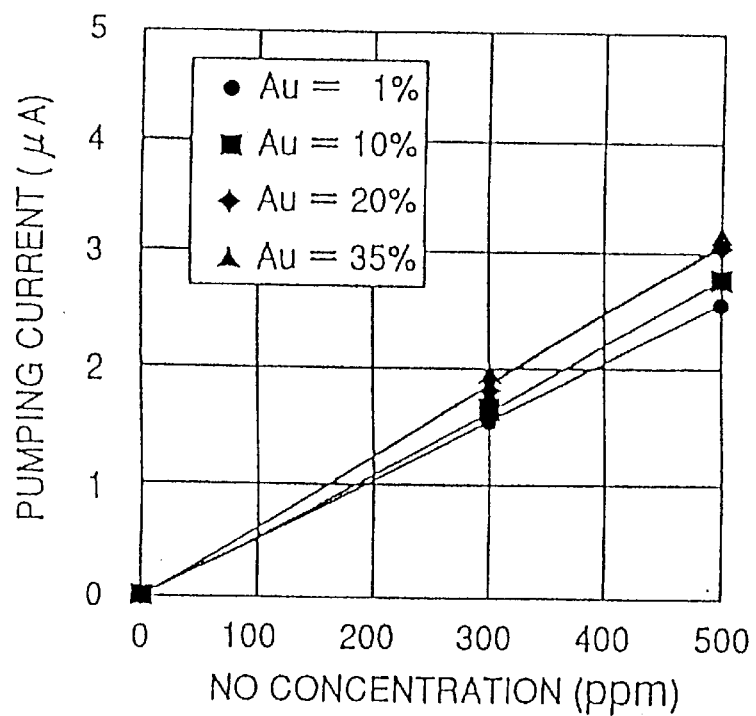

However, the NOx sensitivity (sensitivity to a change in the NOx concentration of the measurement gas) of the sensing element using the 35 wt. % of Au in the Au—Pt electrodes 16, 22 is higher than that of the sensing element using the 1 wt. %-Au alloy, as indicated in the graph of FIG. 27. Described more specifically, the NOx sensitivity of the sensing element using the 35 wt. %-Au alloy is about 20% higher than that of the sensing element using the 1 wt. %-Au alloy. In FIG. 27, the NOx sensitivity is represented by the gradient of the lines representative of the pumping current-NO concentration relationship. This improvement of the NOx sensitivity appears to be derived from a decrease in the NOx reducing ability of the electrodes 16, 22 in the first internal space 6, which results from an increase in the Au content.

Specimen sensing elements were prepared using the electrodes 16 and 22 formed of cermet materials including zirconia and Au—Pt alloys whose Au contents are 1 wt. %, 10 wt. %, 20 wt. %, 35 wt. %, 36 wt. %, 37 wt. %, 38 wt. %, 39 wt. % and 40 wt. %, respectively. An SEM observation of the surfaces of the electrodes of the sensing elements prepared by firing at 1500° C. revealed abnormal growth of grains of the powdered Au—Pt alloys whose Au-contents are 37 wt. % or larger. The sensing elements which suffered from the abnormal grain growth did not normally operate to determine the NOx concentration of the measurement. Further, the electrodes whose Au-contents are 37 wt. % or larger exhibited a higher electrical resistance than the other electrodes whose Au-contents are 36 wt. % or smaller. As indicated in the table below, the electrical resistance of the electrodes increased with an increase in the Au-content from 35 wt. % to 40 wt. %. In view of the above facts, the Au-content of the Au—Pt or Au—Rh alloy should not exceed 36 wt. %.

| Au Content (%) | 1 | 10 | 20 | 35 | 36 | 37 | 38 | 39 | 40 |
|---|---|---|---|---|---|---|---|---|---|
| Abnormal Grain Growth | NO | NO | NO | NO | NO | YES | YES | YES | YES |
| Resistance (Ω) | 9 | 9 | 9 | 9 | 12 | 20 | 28 | 32 | 36 |

The use of the Au alloy consisting of a 0.01–36 wt. % of Au and the balance being substantially Pt or Rh desirably causes significant reduction in the NOx reducing ability of the electrodes 16, 22 disposed in the first internal space 6, even where the oxygen partial pressure of the atmosphere within this space 6 is relatively low. That is, the use of the Au-alloy described above makes it possible to minimize or zero the amount of oxygen to be generated by NOx reduction in the first internal space 6, and to minimize the amount of oxygen in the measurement gas which is to be introduced into the second internal space 8 in which the NOx component of the gas is reduced for determination of the NOx concentration of the measurement gas. Thus, the Au-alloy electrodes 16, 22 are effective to minimize the amount of oxygen which is introduced from the first internal space 6 into the second internal space 8 and which adversely influences the accuracy of determination of the NOx component.

The impedance of the electrochemical pumping cells will increase with an increase in the cumulative operating time of a sensing element. Specimen sensing elements as shown in FIGS. 1 and 2 whose Au-alloys of the inner pumping electrodes 16 of the first pumping cell have different Au contents were operated at 600° C. in a diesel engine exhaust gas, to obtain the cumulative operating time until the impedance of the first pumping cell has increased to a value five times as high as the initial value. Generally, the durability of the sensing element decreases with an increase in the impedance of the pumping cell, since the function of the Au-alloy electrode is more likely to deteriorate due to sintering of the Au alloy at a relatively high value of the cell impedance, particularly when the sensing element is operated at a relatively high temperature.

Figure 28:
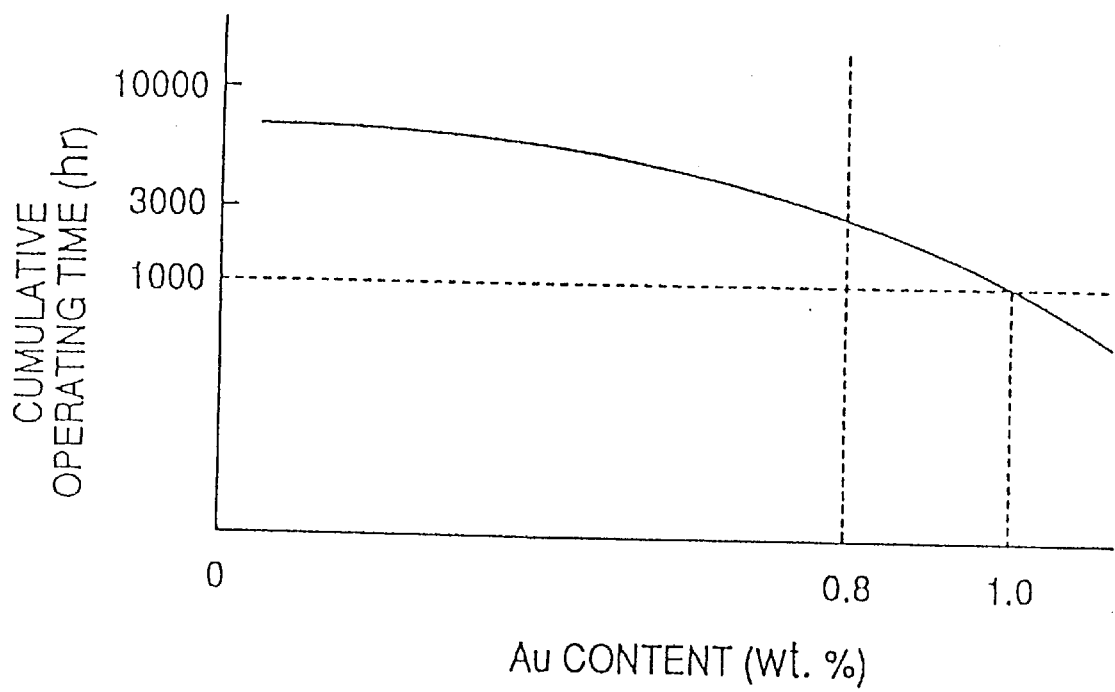
FIGS. 28 and 29 are graphs indicating influences of the Au content of the Au—Pt alloy on the durability of the sensing element and the voltage-current relationship of the first and second pumping cells.

The test showed a relationship between the operating time and the Au content of the Au alloys, as indicated in the graph of FIG. 28. It will be understood from the graph that the durability of the sensing element (expressed by the cumulative operating time) tends to drop to a greater extent when the Au content exceeds 1 wt. %. For increased durability of the sensing element, therefore, the Au content of the Au alloy is preferably not larger than 1 wt. %.

Where the Au-alloy electrode is a cermet electrode including zirconia, for example, the porous structure of the electrode is likely to be plugged due to sintering in the firing or baking process of the appropriate green paste into the porous cermet electrode, if the Au content exceeds 0.8 wt. %. To avoid functional deterioration of the electrode, the Au content is preferably not larger than 0.8 wt. %.

Figure 29:
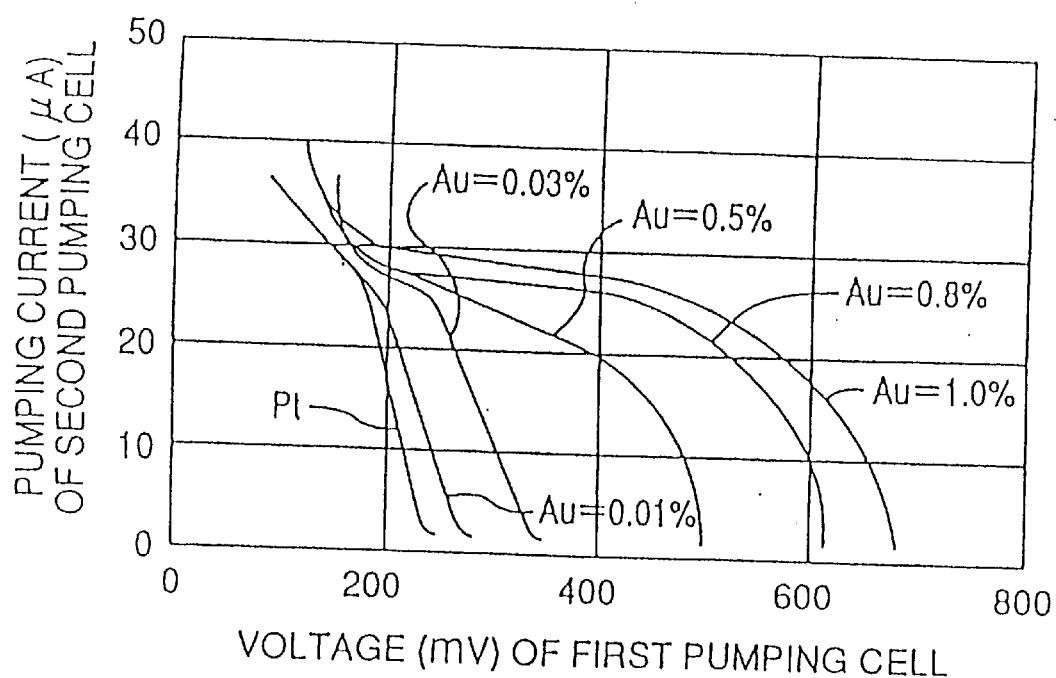

Specimen sensing elements as shown in FIGS. 1 and 2 whose Au—Pt alloys of the electrodes 16, 22 in the first internal space 6 have different Au contents (0%, 0.01%, 0.03%, 0.5%, 0.8% and 1.0%) were operated at 680° C. in a measurement gas consisting of 0.3% of oxygen, 3% of H$_2$O, 500 ppm of NO and the balance being nitrogen, with different voltages being applied to the first pumping cell (including the electrode 16). The pumping current of the second pumping cell including the electrode 28 was measured. A relationship of the voltage of the first pumping cell and the pumping current of the second pumping cell is indicated in the graph of FIG. 29. As is apparent from this graph, the sensing element using the Pt electrode (whose Au content is 0%) has an extremely narrow range of the voltage of the first pumping cell in which the pumping current varies. In other words, where the Au content is smaller than 0.01%, the NOx reducing ability or activity of the electrodes 16, 22 is not reduced enough for the first pumping cell to pump out only the oxygen which is introduced into the first internal space 6 with the measurement gas from the external measurement-gas space, while preventing generation of oxygen by the NOx reduction in the first internal space 6, so as to assure accurate determination of the NOx component on the basis of the oxygen generated by NOx reduction in the second internal space 8. For this reason, the Au content of the Au-alloy electrodes 16, 22 should be 0.01 wt. % or larger, preferably, 0.03 wt. % or larger.

While the use of the Au—Pt alloys for the electrodes 16, 22 is preferable, the Au—Rh alloys may also be used for these electrodes. Further, the Au—Pt or Au—Rh alloys described above may also be used for the inner pumping electrode 28 disposed in the second internal space 8. In this case, a suitable NOx reducing catalyst is desirably provided in the second internal space 8. For example, a porous layer of alumina may be formed as a catalyst so as to cover the electrode 28 containing an Au—Pt or Au—Rh alloy, or in the vicinity of the electrode 28.

Figure 30:
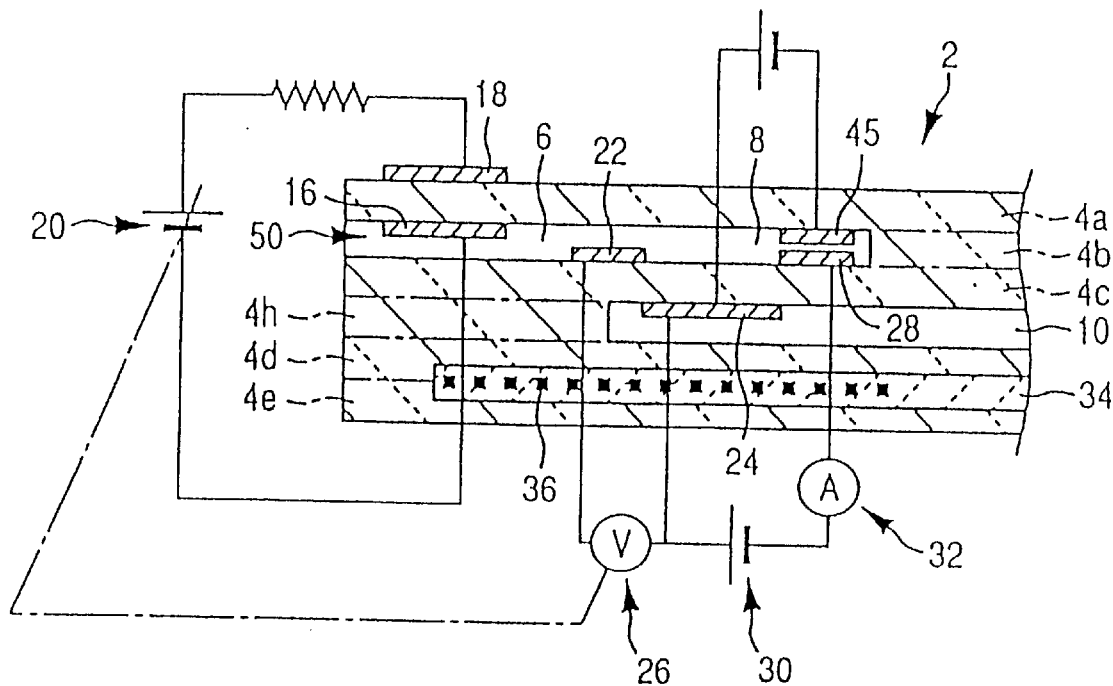
FIG. 30 is an elevational view showing a further embodiment of the sensing element of the invention including an auxiliary pumping cell having a Au—Pt alloy electrode.

The Au—Pt or Au—Rh alloy described above may also be used for an electrode 45 (FIG. 30) which is formed on the oxygen-ion conductive solid electrolyte layer 4a so as to be exposed to the second internal space 8. This electrode 45 cooperates with the solid electrolyte layers 4a–4c and the reference electrode 24 to constitute an auxiliary electrochemical pumping cell, which is adapted to pump the oxygen which has not been pumped out by the first pumping cell and which is introduced into the second internal space 8. The electrode 45 in this instance function as an inner pumping electrode. This auxiliary pumping cell is effective to control the oxygen partial pressure in the second internal space 8 to a predetermined level close to zero, for improving the accuracy of determination of the NOx component irrespective of a variation in the oxygen concentration of the measurement gas.

It is to be understood that the present invention may be otherwise embodied with various other changes, modifications and improvements, which may occur to those skilled in the art, without departing from the scope of the invention as defined in the following claims.

We claim:

1. A method of measuring a concentration of NOx in a measurement gas, comprising the steps of:

introducing the measurement gas containing NOx, into a first internal space under a first diffusion resistance;

controlling an oxygen partial pressure in said first internal space to a level which does not substantially decompose NO;

introducing the atmosphere in said first internal space into a second internal space under a second diffusion resistance;

reducing or decomposing NO present in the atmosphere in said second internal space, so as to produce oxygen; and measuring a concentration of said oxygen produced by reduction or decomposition of NO in said second internal space.

2. The method of claim 1, wherein said step of measuring a concentration of said oxygen produced by reduction or decomposition of NO in said second internal space comprises detecting an electric current flowing through an oxygen pumping cell disposed in said second internal space.

3. The method of claim 1, wherein said level to which said oxygen partial pressure in said first internal space is controlled is substantially negligible.

4. The method of claim 1, wherein said level of said oxygen partial pressure in said first internal space is controlled by an oxygen pumping action of an electrochemical cell.

* * * * *

UNITED STATES PATENT AND TRADEMARK OFFICE
CERTIFICATE OF CORRECTION

PATENT NO : 5,939,615
DATED : August 17, 1999
INVENTOR(S) : Nobuhide KATO and Kunihiko NAKAGAKI It is certified that error appears in the above-identified patent and that said Letters Patent is hereby corrected as shown below:

On title page, item 56 Foreign Patent Documents
replace "1-27751" with --1-277751--.

Signed and Sealed this

Sixteenth Day of January, 2001

Attest:

Attesting Officer

Q. TODD DICKINSON
Commissioner of Patents and Trademarks